US005693470A

United States Patent [19]
de la Chapelle et al.

[11] Patent Number: 5,693,470
[45] Date of Patent: Dec. 2, 1997

[54] DIAGNOSTIC METHOD EMPLOYING MSH2 NUCLEIC ACIDS

[75] Inventors: Albert de la Chapelle, Helsingfors, Finland; Bert Vogelstein; Kenneth W. Kinzler, both of Baltimore, Md.

[73] Assignee: The Johns Hopkins University, Baltimore, Md.

[21] Appl. No.: 457,175

[22] Filed: Jun. 1, 1995

Related U.S. Application Data

[60] Division of Ser. No. 160,295, Dec. 2, 1993, which is a continuation-in-part of Ser. No. 56,546, May 5, 1993, Pat. No. 5,492,808.

[51] Int. Cl.$^6$ .............................. C12Q 1/68; C07H 21/02
[52] U.S. Cl. ........................................ 435/6; 536/23.1
[58] Field of Search ............................ 435/6; 536/22.1

[56] References Cited

U.S. PATENT DOCUMENTS

| 5,075,217 | 12/1991 | Weber . | |
| 5,272,057 | 12/1993 | Smulson et al. | 435/6 |
| 5,330,892 | 7/1994 | Vogelstein et al. | 435/6 |
| 5,382,510 | 1/1995 | Levine et al. | 435/6 |
| 5,401,635 | 3/1995 | Nakamura et al. | 435/6 |

OTHER PUBLICATIONS

Peinado et al. PNAS 89:10,0065–10,069 (1990).
Powell et al. Nature 359: 235–237 (1992).
Päivi Peltomäki, et al., Genetic Mapping of a Locus Predisposing to Human Colorectal Cancer, Science, vol. 260, 7 May 1993 pp. 810–812.
Lauri A. Aaltonen, et al., Clues to the Pathogenesis of Familial Colorectal Cancer, Science, vol. 260, 7 May 1993, pp. 812–816.
S.N. Thibodeau, et al., Microsatellite Instability in Cancer of the Proximal Colon, Science, vol. 260, 7 May 1993, 816–819.
Rick Weise, Gene for Colon Cancer Identified, Scientists Foresee Simple Blood Test for Hereditary Forms of Disease, Washington Post, Dec. 3, 1993.
Richard Fishel, et al., The Human Mutator Gene Homolog MS H2 and Its Association with Hereditary Nonpolyposis Colon Cancer, Cell, vol. 75, 1027–1038, Dec. 3, 1993.
Scc–1, a novel colon cancer susceptibility gene in the mouse: linkage to CD44 (Ly-24,Pgp–1) on chromosome 2, Corina J. A. Moen, et al., Oncogene (1992), 7, 563–566, Macmillan Press Ltd. 1992.
Strand et al., "Destabilization of Tracts of Simple Repetitive DNA in Yeast by Mutations Affecting DNA Mismatch Repair", Nature, 365:274–276 (1993).
Kunkel, "Slippery DNA and Diseases", Nature, 365: 207–208 (1993).
Parsons, et al., "Hypermutability and Mismatch Repair Deficiency in RER+ Tumor Cells", Cell, 75:1227–1236 (1993).

Primary Examiner—W. Gary Jones
Assistant Examiner—Ethan Whisenant
Attorney, Agent, or Firm—Banner & Witcoff, Ltd.

[57] ABSTRACT

The human MSH2 gene, responsible for hereditary non-polyposis colorectal cancer, was identified by virtue of its homology to the MutS class of genes, which are involved in DNA mismatch repair. The sequence of cDNA clones of the human gene are provided, and the sequence of the gene can be used to demonstrate the existence of germ line mutations in hereditary non-polyposis colorectal cancer (HNPCC) kindreds, as well as in replication error+ (RER+) tumor cells.

5 Claims, 10 Drawing Sheets

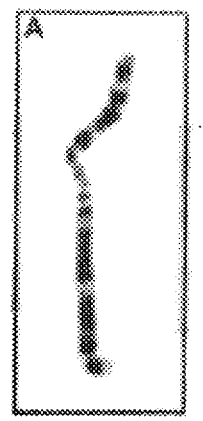 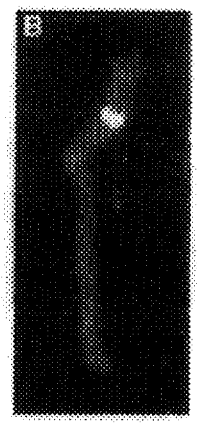 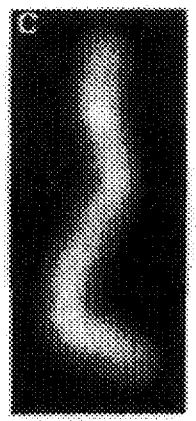 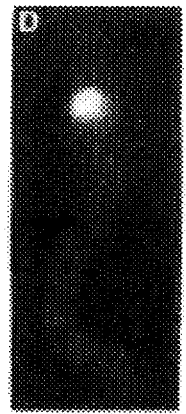
FIG. 2A  FIG. 2B  FIG. 2C  FIG. 2D
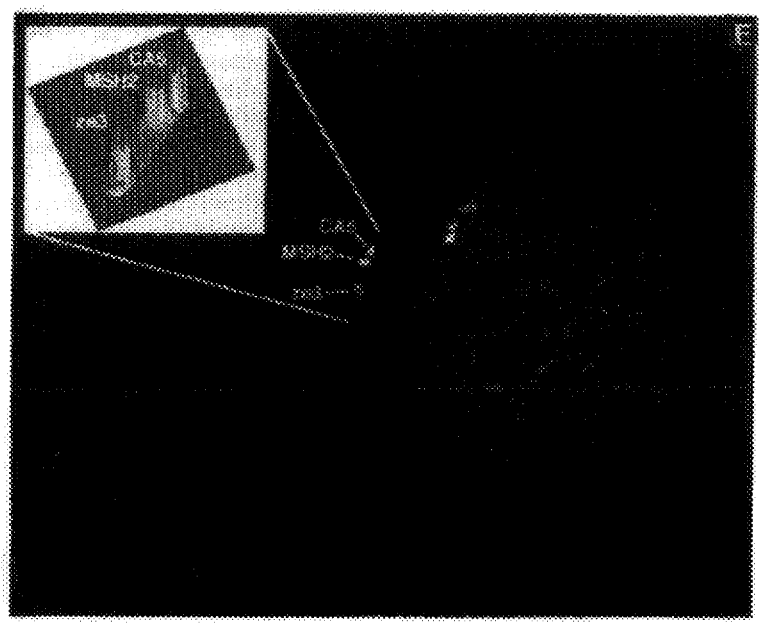
FIG. 2E

FIG. 5A

```
                                                                                                    Met Ala Val Gln Pro
  -68  GG CGG GAA ACA GCT TAG TGG GTG TGG GGT CGC GCA TTT TCT TCA ACC AGG ACG AGG TGA GCA GGT TTC GAC ATG GCG GTG CAG CCG
    6  Lys Glu Thr Leu Gln Leu Glu Ser Ala Ala Glu Val Gly Phe Val Arg Phe Gln Gly Met Pro Glu Lys Pro Thr Thr Thr
   16  AAG GAG ACG CTG CAG TTG GAG AGC GCG GCC GAG GTC GGC TTC GTG CGC TTT CAG GGC ATG CCG GAG AAG CCG ACC ACC ACA
   34  Val Arg Leu Phe Asp Arg Gly Asp Phe Tyr Thr Ala His Gly Glu Asp Ala Ala Arg Glu Val Phe Lys Thr Gln
  100  GTG CGC CTT TTC GAC CGG GGC GAC TTC TAT ACG GCG CAC GGC GAG GAC GCC GCC CGG GAG GTG TTC AAG ACC CAG
   62  Gly Val Ile Lys Tyr Met Gly Pro Ala Gly Ala Lys Asn Leu Gln Ser Val Val Leu Ser Lys Met Asn Phe Glu Ser Phe Val
  184  GGG GTG ATC AAG TAC ATG GGG CCG GCA GGA GCA AAG AAT CTG CAG AGT GTT GTG CTT AGT AAA ATG AAT TTT GAA TCT TTT GTA
   90  Lys Asp Leu Leu Val Arg Gln Tyr Arg Val Tyr Lys Asn Arg Ala Gly Asn Lys Ala Ser Lys Glu Asn Asp Trp
  268  AAA GAT CTT CTT GTT CGT CAG TAT AGA GTT TAT AAG AAT AGA GCT GGA AAT AAG GCA TCC AAG GAG AAT GAT TGG
  118  Tyr Leu Ala Tyr Lys Ala Ser Pro Gly Asn Leu Ser Gln Phe Glu Asp Ile Leu Phe Gly Asn Asn Asp Met Ser Ala Ser Ile
  352  TAT TTG GCA TAT AAG GCT TCT CCT GGT AAC CTT TCT CAG TTT GAA GAC ATT CTC TTT GGT AAC AAT GAT ATG AGT GCT TCC ATT
  146  Gly Val Val Gly Val Val Lys Met Ser Ala Val Asp Gly Tyr Val Gly Tyr Val Asp Ser Ile Gln Arg Gly Leu Arg Lys Leu
  436  GGT GTT GTG GGT GTT AAA ATG TCC GCA GTT GAT GGA TAT GTG GGA TAT GTT GAT TCC ATA CAG AGG GGA AAA CTA
  174  Gly Leu Cys Glu Phe Pro Asp Asn Asp Gln Phe Ser Asn Leu Leu Ala Leu Ile Gly Pro Lys Gly Cys Val Leu
  520  GGA CTG TGT GAA TTC CCT GAT AAT GAT CAG TTC TCC AAT CTT CTT GCT CTC ATT GGA CCA AAG GGA TGT GTT TTA
  202  Pro Gly Gly Glu Thr Ala Gly Asp Met Gly Lys Leu Arg Gln Ile Ile Thr Glu Arg Lys Lys
  604  CCC GGA GGA GAG ACT GCT GGA GAC ATG GGG AAA CTG AGA CAA ATT ATC ACA GAA AGA AAA AAA
  230  Ala Asp Phe Ser Thr Lys Asp Ile Tyr Gln Asn Arg Leu Asn Arg Leu Leu Lys Gly Glu Gln Met Asn Ser Ala Val
  688  GCT GAC TTT TCC ACA AAA GAC ATT TAT CAG AAC CGG TTG AAC AGG CTC TTG AAA AAG GGA GAG CAG ATG AAT AGT GCT GTA
  258  Leu Pro Glu Met Glu Asn Gln Val Ala Val Ser Ser Leu Ser Ala Val Ile Lys Phe Leu Glu Leu Leu Ser Asp Asp Ser Asn
  772  TTG CCA GAA ATG GAG AAT CAG GTT GCA GTT TCT TCT CTG TCA GCA GTT ATC AAG TTT TTA GAA CTC TTA TCA GAT GAT TCC AAC
  286  Phe Gly Gln Phe Glu Leu Thr Thr Phe Asp Phe Ser Gln Tyr Met Lys Leu Asp Ala Ala Val Arg Ala Leu Asn Leu Phe
  856  TTT GGA CAG TTT GAA CTG ACT ACT TTT GAC TTC AGC CAG TAT ATG AAA TTG GAT GCA GCA GTC AGA GCA CTT AAC CTT TTT
```

FIG. 5B

```
314   Gln Gly Ser Val Glu Asp Thr Thr Gly Ser Gln Ala Leu Asn Lys Cys Lys Thr Pro Gly Gln Arg Leu
940   CAG GGT TCT GTT GAA GAT ACC ACT GGC TCT CAG GCT CTG AAT AAG TGT AAA ACC CCT CAA GGA CAA AGA CTT

342   Val Asn Gln Trp Ile Lys Gln Pro Leu Met Asp Lys Asn Arg Ile Glu Val Glu Leu Asn Leu Ala Phe Val Glu Asp
1024  GTT AAC CAG TGG ATT AAG CAG CCT CTC ATG GAT AAG AAC AGA ATA GAG GTT GAA CTT AAT TTA GCC TTT GTA GAA GAT

370   Ala Glu Leu Arg Gln Thr Leu Gln Asp Phe Pro Asn Arg Arg Ile Asp Leu Pro Asn Val Ile Gln Ala Leu Glu Lys Phe Ser Lys Phe Gln Glu Arg Gln
1108  GCA GAA TTG AGG CAG ACT TTA CAA GAT TTC CCA AAT CGA CGA ATA GAT CTA CCT AAT GTT ATA CAG GCT CTG GAA AAG TTT TCC AAG TTT CAA GAA AGA CAA

398   Ala Ala Asn Leu Gln Asp Cys Tyr Arg Leu Tyr Gln Gly Ile Asn Thr Pro Leu Thr Asp Phe Ser Asp Phe Asp Pro Asn Leu Ser Glu Leu
1192  GCA GCA AAC TTA CAA GAT TGT TAC CGA CTC TAT CAG GGT ATA AAT CAA CTA CCT ATT ACT GAC TTC TCT GAT TTT GAT CCT AAT CTC AGT GAA TTA

426   Gly Lys His Gln Leu Leu Leu Ala Val Phe Val Thr Pro Leu Thr Arg Val Lys Pro Ser Ala Ala Arg Asp Leu Asp Gly Leu Asp Pro Gly Lys
1276  GGA AAA CAC CAG TTA TTG TTG GCA GTT TTT GTG ACT CCT CTT ACT CGT GTA AAA CCT TCA GCA GCC AGA GAT CTT GAC GGC TTG GAC CCT GGC AAA

454   Ile Glu Thr Thr Leu Asn His Glu Phe Leu Val Lys Met Gln Val Glu Phe Ser Thr Leu Ile Ile Ser Ala Arg Asp Leu Gly Glu Lys Val Leu Arg Asn Ile Thr Lys
1360  ATA GAA ACA ACT TTA AAT CAT GAA TTC CTT GTA AAA ATG CAG GTG GAA TTC TCA ACA TTA ATA ATA AGT GCA AGA GAT CTT GGC GAG AAA GTC CTT CGT AAT ATT ACC

482   Arg Glu Ile Met Asn Leu Glu Gly Lys Lys Met Ser Lys Phe Tyr Phe Arg Val Thr Cys Lys Glu Glu Ile Glu Tyr Thr Lys
1444  AGA GAA ATA ATG AAT CTT GAA AAG AAG ATG TCA AAG TTC TAC TTT CGT GTA ACC TGT AAA GAA GAA ATT TAC ACC AAA

510   Gln Ile Lys Leu Asp Ser Ser Ala Gln Phe Gly Tyr Val Lys Phe Thr Asn Asn Ser Leu Leu Phe Ala Ile Ser Ser Gly Tyr Val Glu Pro Met Gln
1528  CAG ATT AAA CTG GAT AGT TCC AGT GCA CAG TTT GGA TAT GTA AAG TTT ACC AAC AAC AGC CTT TTG TTT GCT ATT TCT TCA GGC TAT GTA GAA CCA ATG CAG

538   Asn Phe Ser Thr Val Asp Ile Gln Lys Asn Gly Val Lys Val Asn Ile Val Ser Asn Gly His Val Ser Phe Ala Pro Val Pro Tyr Val Arg
1612  AAC TTT AGT ACT GTA GAT ATC CAG AAG AAT GGT GTT AAA GTG AAT ATT GTC AGC AAT GGG CAT GTG TCA TTT GCT CCT GTT CCA TAT GTA CGA

566   Asn Lys Thr Glu Tyr Gln Leu Ala Gln Leu Ala Val Val Ser Phe Ala His Ala Cys Leu Lys Ala Ser Arg His Ala Ser Ile Leu Lys Ala Ile Ala
1696  AAT AAA ACA GAA TAT CAA CTA GCT CAG CTA GCT GTT GTC AGC TTT GCT CAC GCT TGT CTA AAA GCA TCC AGG CAT GCA TCC ATA TTA AAA GCA ATT GCA

594   Thr Leu Asn Asp Val Leu Gly Arg Ile Ile Leu Lys Ala Cys Val Glu Val Gln Asp Glu Ile Ala
1780  ACA CTC AAT GAT GTG TTA GGC AGA ATT ATA TTA AAA GCA TGT GTT GAA GTT CAA GAT GAA ATT GCA

622   Pro Ala Ile Leu Glu Lys Gly Gln Gly Arg Ile Ile Leu Lys Ala Cys Val Glu Val Gln Asp Glu Ile Ala
1864  CCA GCA ATT TTG GAG AAA GGA CAA GGA AGA ATA ATT TTA AAA GCA TGT GTT GAA GTT CAA GAT GAA ATT GCA
```

FIG. 5C

| | | | | | | | | | | | | |
|---|---|---|---|---|---|---|---|---|---|---|---|---|
| 650 | Phe | Ile | Pro | Asn | Asp | Val | Tyr | Phe | Glu | Lys | Asp | ... Ser Thr |
| 1948 | TTT | ATT | CCT | AAT | GAC | GTA | TAC | TTT | GAA | AAA | GAT | ... TCA ACA |
| 678 | Tyr | Ile | Arg | Gln | Thr | Gly | Val | Ile | Val | Leu | Met | ... Ile Val |
| 2032 | TAT | ATT | CGA | CAA | ACT | GGG | GTG | ATA | GTA | CTC | ATG | ... ATT GTG |
| 706 | Asp | Cys | Ile | Leu | Ala | Arg | Val | Gly | Ala | Gly | Asp | ... Thr Ala |
| 2116 | GAC | TGC | ATC | TTA | GCC | CGA | GTA | GGG | GCT | GGT | GAC | ... ACT GCT |
| 734 | Ser | Ile | Leu | Arg | Ser | Ala | Thr | Lys | Asp | Ser | Leu | ... Phe Gly |
| 2200 | TCT | ATC | CTC | AGG | TCT | GCA | ACC | AAA | GAT | TCA | TTA | ... TTT GGG |
| 762 | Leu | Ala | Trp | Ala | Ile | Ser | Glu | Tyr | Ile | Ala | Thr | ... Thr Ala |
| 2284 | TTA | GCA | TGG | GCT | ATA | TCA | GAA | TAC | ATT | GCA | ACA | ... ACT GCC |
| 790 | Leu | Ala | Asn | Gln | Ile | Pro | Thr | Val | Asn | Asn | Leu | ... Gln Val |
| 2368 | TTG | GCC | AAT | CAG | ATA | CCA | ACT | GTT | AAT | AAT | CTA | ... CAG GTG |
| 818 | Lys | Lys | Gly | Val | Cys | Asp | Gln | Ser | Phe | Gly | Ile | ... Ala Lys |
| 2452 | AAG | AAA | GGT | GTC | TGT | GAT | CAA | AGT | TTT | GGG | ATT | ... GCT AAA |
| 846 | Gln | Lys | Ala | Leu | Glu | Arg | Glu | Gln | Gly | Ser | Gln | ... Lys Cys |
| 2536 | CAG | AAA | GCC | CTG | GAA | AGA | GAG | CAG | GGT | TCG | CAA | ... AAG TGC |
| 874 | Tyr | Leu | Glu | Phe | Leu | Lys | Gln | Phe | Leu | Ser | Lys | ... Ser Glu |
| 2620 | TAT | CTG | GAA | TTC | CTG | AAG | CAG | TTC | CTG | TCC | AAG | ... TCA GAA |
| 902 | Glu | Asn | Ile | Thr | Ile | Lys | Leu | Lys | Gln | Leu | Ala | ... Ser Arg |
| 2704 | GAA | AAC | ATC | ACA | ATA | AAG | TTA | AAA | CAG | CTA | GCT | ... TCA CGA |
| 930 | Ile | Lys | Val | Thr | Thr | | | | | | | |
| 2788 | ATA | AAA | GTT | ACT | ACG | TGA | AAA | ATC | CCA | GTA | ATG | ... ATA TTG TTT |
| 2872 | TAT | ATT | AA | | | | | | | | | |

FIG. 6A

```
hMSH2  iavqpketlqlesaafvgfvrfqsmpertt VRLF DRGDFYTAH EEDALLA REVFK TQGVIK ymgpagaknlqsvvl    80
yMSH2  isstrpelkfs VSEE RN YRKL TCLPK KLK TIRL VDKGDY YTVIES DAIFVADS VYH TQSVLK ncqldpvtaknfhep  80 hMSH2  elmnfes fvkdll lveqyrv qvyknragnkas k ENDWYLAY KASEG NLSF EDI LFGNNDA SAS IGVVGVK MSAVE EQRQ  160
yMSH2  ekvytvelqvlatil iklcll elgykveiy---- DKGAN IKS ASP GNIEV NELN MMIDSSI I IASLK IQWNSQ DENCI  156 hMSH2  vgvgyv DSIQRKLE LC EF PNDQF SNL EALLI Cl SPKE CVL----PGGET ACD YGKLRQIIQRGSI LI TERKK ADE STKD  236
yMSH2  igva fiditay rveml diVDNE VSN LESFL QLGVEG Lvqd ltsnsnae vq kvin vidr cgc vv illen sefsekd  236 hMSH2  i yqd en rliL kgkkgeqmnsavlpe menqvavss ls av ik flels ddsnf qo fe ltfds qy klidi aav rain ll qgs    316
yMSH2  vel de tklilgddlals------lpqkysklsmgacnalig vlql seq dqv ekibl vehkklke fvkkld asai kalnl fpqg  311 hMSH2  vedtt gsqslaa--------------llnk kvl po qs rlv nglm ikqp emq ok nrieerlnlvea fveda elroti oed  379
yMSH2  pqmpf ssnn lavsgftsagnsgkvtslfqe lan hckn ag vri lnemlk odin ide lnkrhdl vdy lidqie lrom ltse  391 hMSH2  lerrfeelnrilaksfqr qaanlqdcyr liqgi nqlenvi qalekheghqk-----illa vfvt plidl rsdfsk fqem     453
yMSH2  yl pmidirrltk kllnkr-gn leed vlni ko fs kri feiv vfts fledds ptepvne lvrsv mla plsh hvep lsk feen  470 hMSH2  ietvlldmdqvenhe-fl vn ps fl pnl selrei mndekkm qs tli saardlgldpg kqi kids saqfs yyfrv ckekv    532
```

FIG. 6B

```
yMSH2  METTVDLDAYSENNeFMIKVEENEELGKIDSKLETTRDEIHSIHLDSAEDLGFDPDKKLNLENHHLHSNCMRLTRNDAKE      550
hMSH2  LRNNMFSTVDIQNGVAFINSKLETSLNEEYTQNKTEYEEAQDAIVKEIVNISSGHVEPMQTLNDVLAQLDAVVSFAHVS      612
yMSH2  LRHIKVIELSTVKAGIFESTKQLKSIANETNILQKEYDKQQSALURETNNVLTLTPVFEKISLVLAHLDVIASFAHTS      630
hMSH2  NGAPVPYVRPailekgqg-RIIEKASRHEACVEVQDEIAFIPNDVYFEKDIQMEHILITGPNMGGKSTYIRQTGVIVLMAQI      691
yMSH2  SYAPIPYIIREklhpmdserTRHLISSRHPVLDMQDDISFISNDVTLESGKGDFLIITGPNMGGKSTYIRQVGVISLMAQI      710
hMSH2  GCFVPCESAEVSIVDCILARVGAGDSQLKGVSTFMADMLETASILRSATKDSLIIIDELGRGTSTYDGFGLAWAISEYIA      771
yMSH2  GCFVPCEEAEIAIVDAILCRVGAGDSQLKGVSTFMVEILETASILKNASKNSLIIVDELGRGTSTYDGFGLAWAIASHIA      790
hMSH2  TRIGAFCMEATHFHELTALANQIETNMNLAHVTAltt-------EETLTMLYQLKKGVCDQSEGIHVAELANFPKHVIE      842
yMSH2  SKIGCFALFATHFHELTELSEKLPNVKNMHVVThieknlkeqkhdDEDITLLYKVEPFISDQSFGIHVAEVVQFEKIVK      870
hMSH2  CAKQKALELEEFQYIGESqgqydiNepaakkcyleSqggekiiqeflsRvkqmpftemseGnidiklkSlkaeviLnknsf      922
yMSH2  MARRKGNELDDLKTNNEDlkkakILslqevnegniFlkallkewirkvNeegLhdpskitReeaSqhkiSellraZanepek   950
hMSH2  vnSiisrIkvEt----                                                                  934
yMSH2  enThyleHyKSpccyn                                                                  966
```

DIAGNOSTIC METHOD EMPLOYING MSH2 NUCLEIC ACIDS

This application is a divisional of application Ser. No. 08/160,295, filed Dec. 2, 1993, which is a continuation-in-part of application Ser. No. 08/056,546, filed May 5, 1993 (now U.S. Pat. No. 5,492,808).

This invention was made using U.S. government grants from the NIH CA47527, CA09320, GM26449, CA09243, CA41183, CA42705 CA57435, and CA35494, as well as grants from the Department of Energy DOE/ERN/F139 and DE-FG 09291ER-61139. Therefore the U.S. government retains certain rights to the invention.

TECHNICAL FIELD OF THE INVENTION

The invention relates to a gene which predisposes individuals to colorectal and other cancers. In addition, it also relates to biochemical tests which can be used to identify drugs for treatment of affected individuals.

BACKGROUND OF THE INVENTION

HNPCC (Lynch syndrome) is one of the most common cancer predisposition syndromes, affecting as many as 1 in 200 individuals in the western world (Lynch et al., 1993). Affected individuals develop tumors of the colon, endometrium, ovary and other organs, often before 50 years of age. Although the familial nature of this syndrome was discovered nearly a century ago (Warthin et al., 1913), the role of heredity in its causation remained difficult to define (Lynch et al., 1966). Recently, however, linkage analysis in two large kindreds demonstrated association with polymorphic markers on chromosome 2 (Peltomaki et al., 1993a). Studies in other families suggested that neoplasia in a major fraction of HNPCC kindreds is linked to this same chromosome 2p locus (Aaltonen et al., 1993).

HNPCC is defined clinically by the occurrence of early-onset colon and other specific cancers in first degree relatives spanning at least two generations (Lynch et al., 1993). The predisposition is inherited in an autosomal dominant fashion. It was initially expected that the gene(s) responsible for HNPCC was a tumor suppressor gene, as other previously characterized cancer predisposition syndromes with this mode of inheritance are caused by suppressor gene mutations (reviewed in Knudson, 1993). But the analysis of tumors from HNPCC patients suggested a different mechanism. Most loci encoding tumor suppressor genes undergo somatic losses during tumorigenesis (Stanbridge, 1990). In contrast, both alleles of chromosome 2p loci were found to be retained in HNPCC tumors (Aaltonen et al., 1993). During this search for chromosome 2 losses, however, it was noted that HNPCC tumors exhibited somatic alterations of numerous microsatellite sequences.

Widespread, subtle alterations of the cancer cell genome were first detected in a subset of sporadic colorectal tumors using the arbitrarily-primed polymerase chain reaction (Peinado et al., 1992). These alterations were subsequently found to represent deletions of up to 4 nucleotides in genomic polyA tracts (Ionov et al., 1993). Other studies showed that a similar, distinctive subgroup of sporadic tumors had insertions or deletions in a variety of simple repeated sequences, particularly microsatellite sequences consisting of dinucleotide or trinucleotide repeats (Ionov et al., 1993; Thibodeau et al., 1993; Aaltonen et al., 1993). Interestingly, these sporadic tumors had certain features in common with those developing in HNPCC kindreds, such as a tendency to be located on the right side of the colon and to be near-diploid. These and other data suggested that HNPCC and a subset of sporadic tumors were associated with a heritable defect causing replication errors (RER) of microsatellites (Ionov et al., 1993; Aaltonen et al., 1993).

The mechanism underlying the postulated defect could not be determined from the study of tumor DNA, but studies in simpler organisms provided an intriguing possibility (Levinson and Gutman, 1987; Strand et al., 1993). This work showed that bacteria and yeast containing defective mismatch repair genes manifest instability of dinucleotide repeats. The disruption of genes primarily involved in DNA replication or recombination had no apparent effect on the fidelity of microsatellite replication (reviewed in Kunkel, 1993). These pivotal studies suggested that defective mismatch repair might be responsible for the microsatellite alterations in the tumors from HNPCC patients (Strand et al., 1993).

Thus there is a need in the art to identify the actual gene and protein responsible for hereditary non-polyposis colorectal cancer and the replication error phenotype found in both hereditary and sporadic tumors. Identification of the gene and protein would allow more widespread diagnostic screening for hereditary non-polyposis colorectal cancer than is currently possible. Identification of the involved gene and protein would also enable the rational screening of compounds for use in drug therapy of hereditary non-polyposis colorectal cancer, and would enable gene therapy for affected individuals.

SUMMARY OF THE INVENTION

It is an object of the invention to provide a DNA molecule which when mutated is the genetic determinant for hereditary non-polyposis colorectal cancer.

It is another object of the invention to provide DNA molecules which contain specific mutations which cause hereditary non-polyposis colorectal cancer.

It is yet another object of the invention to provide methods of treating persons who are predisposed to hereditary non-polyposis colorectal cancer.

It is still another object of the invention to provide methods for determining a predisposition to cancer.

It is a further object of the invention to provide methods for screening test compounds to identify therapeutic agents for treating persons predisposed to hereditary non-polyposis colorectal cancer.

It is still another object of the invention to provide a protein which is important for human DNA mismatch repair.

It is yet another object of the invention to provide a transgenic animal for studying potential therapies for hereditary non-polyposis colorectal cancer.

These and other objects of the invention are provided by one or more of the embodiments described below. In one embodiment of the invention an isolated and purified DNA molecule is provided. The molecule has a sequence of at least about 20 nucleotides of hMSH2, (human analogue of bacterial MutS and *Saccharomyces cerevisiae* MSH2) as shown in SEQ ID NO: 1.

In another embodiment of the invention an isolated and purified DNA molecule is provided. The DNA molecule has a sequence of at least about 20 nucleotides of an hMSH2 allele found in a tumor wherein said DNA molecule contains a mutation relative to hMSH2 shown in SEQ ID NO: 1.

In yet another embodiment of the invention a method of treating a person predisposed to hereditary non-polyposis colorectal cancer is provided. The method prevents accumulation of somatic mutations. The method involves administering a DNA molecule which has a sequence of at least about 20 nucleotides of hMSH2, as shown in SEQ ID NO: 1, to a person having a mutation in an hMSH2 allele which predisposes the person to hereditary non-polyposis colorectal cancer, wherein said DNA molecule is sufficient to remedy the mutation in an hMSH2 allele of the person.

In another embodiment of the invention a method is provided for determining a predisposition to cancer. The method involves testing a body sample of a human to ascertain the presence of a mutation in hMSH2 which affects hMSH2 expression or hMSH2 protein function, the presence of such a mutation indicating a predisposition to cancer.

In still another embodiment of the invention a method is provided for screening to identify therapeutic agents which can prevent or ameliorate tumors. The screening method involves contacting a test compound with a purified hMSH2 protein or a cell; determining the ability of the hMSH2 protein or the cell to perform DNA mismatch repair, a test compound which increases the ability of said hMSH2 protein or said cell to perform DNA mismatch repair being a potential therapeutic agent.

In another embodiment of the invention an isolated and purified protein is provided. The protein has the sequence shown in SEQ ID NO:2.

In still another embodiment of the invention a transgenic animal is provided. The transgenic (nonhuman) animal maintains an hMSH2 allele in its germline. The hMSH2 allele is one which is found in humans having hereditary non-polyposis colorectal cancer or in RER+ tumors. Also provided are animals which have no wild-type MSH2 alleles, due to mutations introduced.

Thus the present invention provides the art with the sequence of the gene responsible for hereditary non-polyposis colorectal cancer and information regarding the mechanism by which it causes tumors. This enables the an to practice a variety of techniques to identify persons at risk of developing a variety of cancers and to treat them to prevent such cancers from actually developing.

PCR was used to determine whether each of the listed markers was present (black box) or absent (white box)in the indicated hybrid. The laboratory name of each hybrid and the formal name (in parentheses) is listed. The hybrid panel was also validated with ten additional polymorphic markers outside of the 136–177 region. M: hybrid derived from microcell-mediated chromosome 2 transfer; T: derived from t(X;2) translocation; X: derived from X-irradiated chromosome 2 donor. MO: mouse-human hybrid; HA: hamster-human hybrid; RA: rat-human hybrid; TEL: telomere; CEN: centromere.

FIGS. 2A–2E show a FISH analysis which was used to determine the proximity and ordering of DNA sequences within chromosome band 2p FIGS. 2A and 2B show FISH mapping of the 123 marker. FIG. 2A shows G-banded menphase chromosome 2. FIG. 2B shows identical chromosome as in FIG. 2A following FISH with a biotin-labeled P1 clone for the 123 marker. Results localize the 123 maker to chromosome band 2p16.3. FIGS. 2C and 2D show co-hybridization documenting the coincident localization of a microdissection (Micro-FISH) probe from chromosome 2p16 and the 123 marker. FIG. 2C shows DAPI stained metaphase chromosome 2. FIG. 2D shows simultaneous hybridization of the biotin-labeled 123 probe (appearing as an intensely staining smaller circle) and the Spectrum-Orange labeled 2p16 Micro-FISH probe (appearing as a diffusely staining larger circle). FIG. 2E shows a representative example of an interphase nucleus simultaneously hybridized with P1 clones for CA5, hMSH2 and ze3. The results were used to directly measure the distances between markers in order to establish the order and relative distance between markers (after Trask et al., 1989). Inset: The image processing program NIH Image was used to provide an average gray value displayed as a surface plot to support the length measurements and to graphically illustrate the relative order information. The surface plot presented defines the specified interphase chromosome and the relative order CA-MSH2-ze3.

Figure 3:
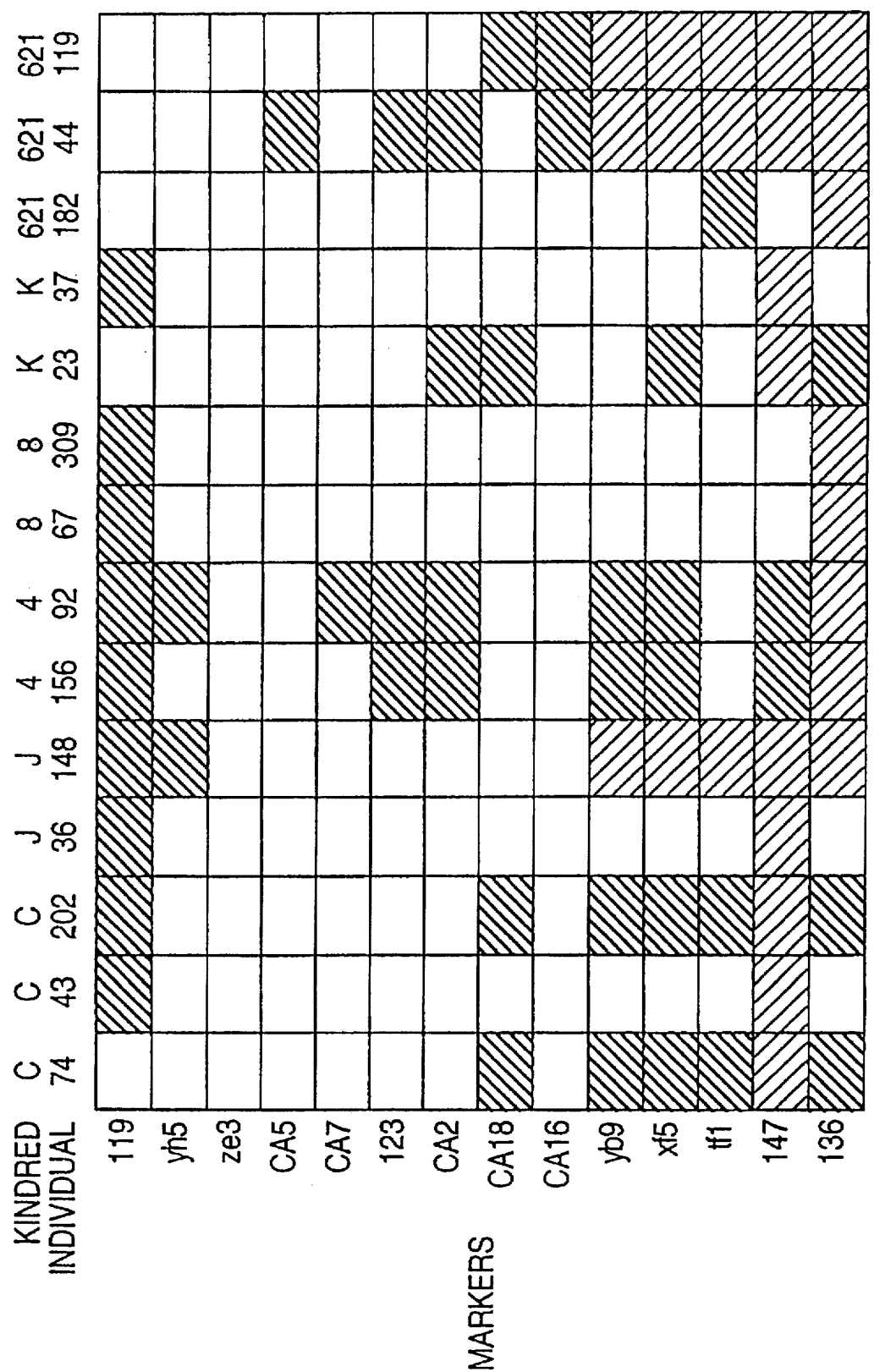
Figure 4A:
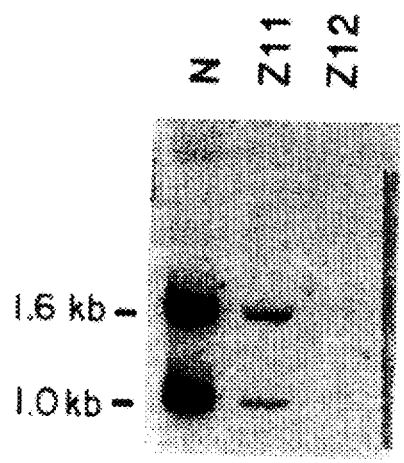
Figure 4B:
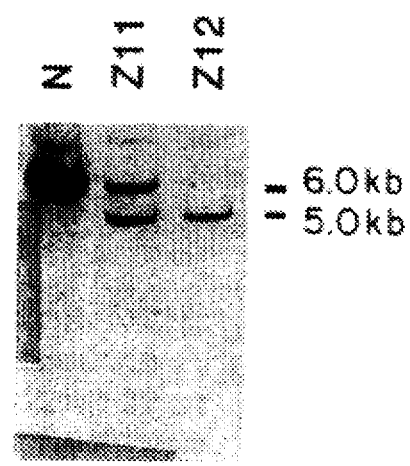
Figure 4C:
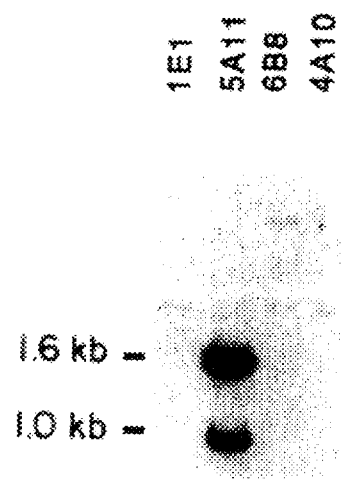
Figure 4D:
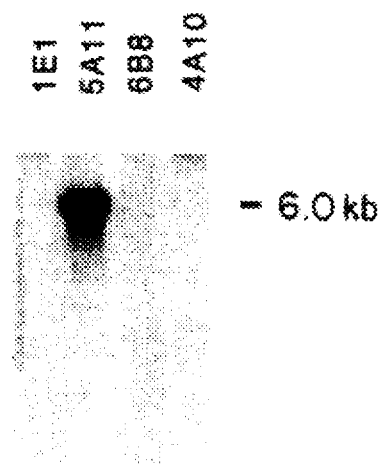

FIG. 3 shows linkage analysis of HNPCC pedigrees.

All affected individuals in which meiotic recombination occurred between markers 119 and 136 are included. A black box indicates that the individual did not contain the allele associated with disease in his/her family or that the individual inherited an allele not associated with disease from his/her affected parent. A white box indicates that the individual had an allele which was the same size as the disease-associated allele. A hatched circle indicates that the marker was not studied. All individuals had colon or endometrial cancer at less than 55 years of age, or had progeny with such disease but did not indicate that the patient necessarily had disease-associated alleles because phase could usually not be determined.

FIGS. 4A–4D show hMSH2 gene localization.

Southern blots containing EcoRI (FIGS. 4A and 4C) and PstI (FIGS. 4B and 4D) digested DNA from the indicated somatic cell hybrids (FIGS. 4A and 4B) or YAC clones (FIGS. 4C and 4D) were hybridized with a radiolabelled insert from cDNA clone pNP-23. Southern blotting and hybridization were performed as described (Vogelstein et al., 1987). Autoradiographs are shown. The 5.0 kb PstI fragment in hybrids Z11 and Z12 is derived from hamster DNA.

FIGS. 5A–C show the cDNA sequence of hMSH2.

An open reading frame (ORF) begins at nucleotide 1 and ends at nt 2802. The predicted amino acid sequence is shown. The sequence downstream of nt 2879 was not determined.

FIGS. 6A and 6B show homology between yeast and human MSH2 genes.

The predicted amino acid sequences of yeast (y) MSH2 (Reenan and Kolodner, 1992) and human MSH2 genes are compared within the region of highest homology. Bloch of similar amino acids are shaded.

FIG. 7 (panel 7A, 7B and 7C) shows germline and somatic mutations of hMSH2.

Figures 7A, 7B, 7C:
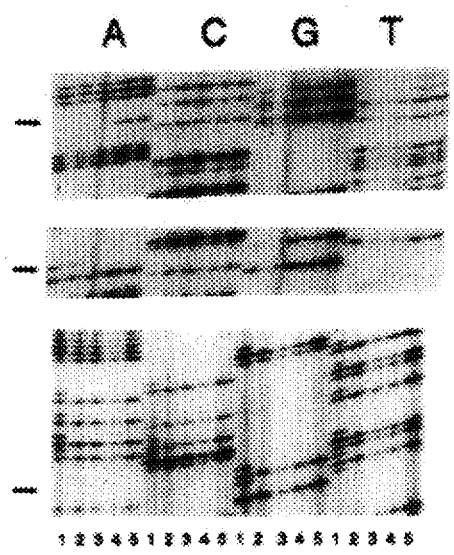

Autoradiographs of polyacrylamide gels containing the sequencing reactions derived from PCR products are shown. The 1.4 kb PCR products containing a conserved region of hMSH2 were generated from genomic DNA samples as described in the Examples. Antisense primers were used in the sequencing reactions. The ddA mixes from each sequencing reaction were loaded in adjacent lanes to facilitate comparison, as were those for C, G, and T. The DNA samples were derived from the tumor (lane 1) and normal colon (lane 2) of patient Cx10, an RER− colon tumor cell line (lane 3), and lymphocytes of patients J42 (lane 4) and J-143 (lane 5). FIG. 7A: A transition (C to T at codon 622) in lymphocyte DNA can be observed in HNPCC patients J42 and J-143. FIG. 7B: A transition (C to T at nt codon 639) in tumor (lane 1) and normal colonic mucosa (lane 2) of patient Cx10. FIG. 7C: A substitution of a TG dinucleotide for an A at codon 663 can be observed in DNA of the tumor of patient Cx10, (lane 1), but not in DNA from her normal colon (lane 2). Arrows mark the substitutions in FIG. 7A and B and the TG dinucleotide insertion site in FIG. 7C.

DETAILED DESCRIPTION OF THE PREFERRED EMBODIMENT

The disclosure of application Ser. No. 08/056,546, filed May 5, 1993, is expressly incorporated herein.

It is a discovery of the present invention that the gene responsible for hereditary non-polyposis colorectal cancer is hMSH2, a human analog of bacterial MutS. The cDNA sequence of hMSH2 is shown in SEQ ID NO: 1. This gene encodes a DNA mismatch repair enzyme. Mutation of the gene causes cells to accumulate mutations. For example, the observed replication error phenotype (RER$^+$) found in both sporadic and hereditary non-polyposis colorectal cancer consists of variations (insertions and deletions) in microsatellite DNA. In yeast and bacteria defective MutS-related genes cause other types of mutations as well.

Useful DNA molecules according to the invention are those which will specifically hybridize to hMSH2 sequences. Typically these are at least about 20 nucleotides in length and have the nucleotide sequence as shown in SEQ ID NO: 1. Such molecules can be labeled, according to any technique known in the art, such as with radiolabels, fluorescent labels, enzymatic labels, sequence tags, etc. According to another aspect of the invention, the DNA molecules contain a mutation which has been found in tumors of HNPCC patients or in sporadic RER$^+$ tumors. Such molecules can be used as allele-specific oligonucleotide probes to track a particular mutation through a family.

According to some aspects of the invention, it is desirable that the DNA encode all or a part of the hMSH2 protein as shown in SEQ ID NO:2. To obtain expression of the protein the DNA sequence can be operably linked to appropriate control sequences, such as promotor, Kozak consensus, and terminator sequences.

A person who is predisposed to develop cancers due to inheritance of a mutant hMSH2 allele can be treated by administration of a DNA molecule which contains all or a part of the normal hMSH2 gene sequence as shown in SEQ ID NO: 1. A portion of the gene sequence will be useful when it spans the location of the mutation which is present in the mutant allele, so that a double recombination event between the mutant allele and the normal portion "corrects" the defect present in the person. A portion of the gene can also be usefully administered when it encodes enough of the protein to express a functional DNA mismatch repair enzyme. Such a portion need not necessarily recombine with the mutant allele, but can be maintained at a separate locus in the genome or on an independently replicating vector. Means for administering DNA to humans are known in the art, and any can be used as is convenient. A variety of vectors are also known for this purpose. According to some techniques vectors are not required. Such techniques are well known to those of skill in the art.

Also contemplated as part of the present invention is the use of a combined anti-neoplastic therapy regimen. Such a combined regimen is useful for patients having an RER$^+$ tumor, whether sporadic or associated with HNPCC. The regimen combines any standard anti-neoplastic therapy to which a patient can become resistant and hMSH2 gene therapy, as described above. By remedying the defect present in RER$^+$cells, i.e., an hMSH2 mutation, the likelihood of the tumor developing a resistance mutation is greatly diminished. By delaying or preventing the onset of resistance, the life of cancer patients can be prolonged. In addition, such prevention of resistance allows a greater degree of tumor destruction by the therapeutic agent. Examples of anti-neoplastic therapies which can be combined with hMSH2 gene therapy are hormones, radiation, cytotoxic drugs, cytotoxins, and antibodies.

Body samples can be tested to determine whether the hMSH2 gene is normal or mutant. Mutations are those deviations from the sequence shown in SEQ ID NO: 1 which are associated with disease and which cause a change in hMSH2 protein function or expression. Such mutations include nonconservative amino acid substitutions, deletions, premature terminations and frameshifts. See Table I. Suitable body samples for testing include those comprising DNA, RNA, or protein, obtained from biopsies, blood, prenatal, or embryonic tissues, for example.

Provided with the information that the defect causing HNPCC and sporadic RER$^+$ tumors is in a DNA mismatch repair enzyme, one can perform assays on test compounds and compositions to determine if they will remedy the defect. Such therapeutic compounds could bind to missense hMSH mutant proteins to restore the proteins to the normal, active conformation. Alternatively such therapeutic compounds could stimulate the expression of alternate pathways for mismatch repair. Screening for such therapeutic compounds could be performed by contacting test compounds with cells, either normal or those with an hMSH2 mutation found in a tumor. The ability of the cells which were contacted with the test compounds is compared with the ability of the same cells which were not contacted for mismatch repair activity. Such activity can be tested as is known in the art. See, for example, Levinson and Gutman, 1987, and Strand et al., 1993. Observation of changes in microsatellite DNA in cells is one way of assessing mismatch repair activity. Another approach is to assay DNA mismatch repair in vitro in nuclear extracts. See Holmes, 1990; Thomas, 1991; and Fang, 1993.

TABLE I

| Sample | Source | Type | Codon | cDNA Nucleotide Change | Predicted Coding Change |
|---|---|---|---|---|---|
| Family J | HNPCC Kindred | Germline | 622 | CCA to CTA | Pro to Leu |
| Family C | HNPCC Kindred | Germline | 265–314 | 793 to 942 Deletion | Inframe Deletion |
| Family 8 | HNPCC Kindred | Germline | 406 | CGA to TGA | Arg to Stop |
| C × 10 | RER + Tumor | Germline | 639 | CAT to TAT | His to Tyr |
|  |  | Somatic | 663 | ATG to TGTG | Frameshift |

Provided with the cDNA sequence and the amino acid of hMSH2 protein, one of ordinary skill in the art can readily produce hMSH2 protein, isolated and purified from other human proteins. For example, recombinant cells or organisms can be used to produce the protein in bacteria, yeast, or other convenient cell system. The isolated and purified protein can be used in screening for new therapeutic agents, for example, in in vitro assays of DNA mismatch repair. The protein can also be used to raise antibodies against hMSH2. Therapeutic administration of the protein is also contemplated.

Transgenic animals are also contemplated by the present invention. These animals would have inserted in their germline hMSH2 alleles which are associated with HNPCC or sporadic tumors. Such animals could provide model systems for testing drugs and other therapeutic agents to prevent or retard the development of tumors. Also contemplated are genetically engineered animals which contain one or more mutations in their own MSH2 genes. The mutations will be engineered to correspond to mutations found in hMSH2 alleles which are found in HNPCC-affected individuals or in other human RER+ tumors. Animals with both native MSH2 alleles inactivated and containing a human wild-type or mutant hMSH2 allele are particularly desirable.

EXAMPLES

Example 1

Somatic Cell Hybrids

Figure 1:
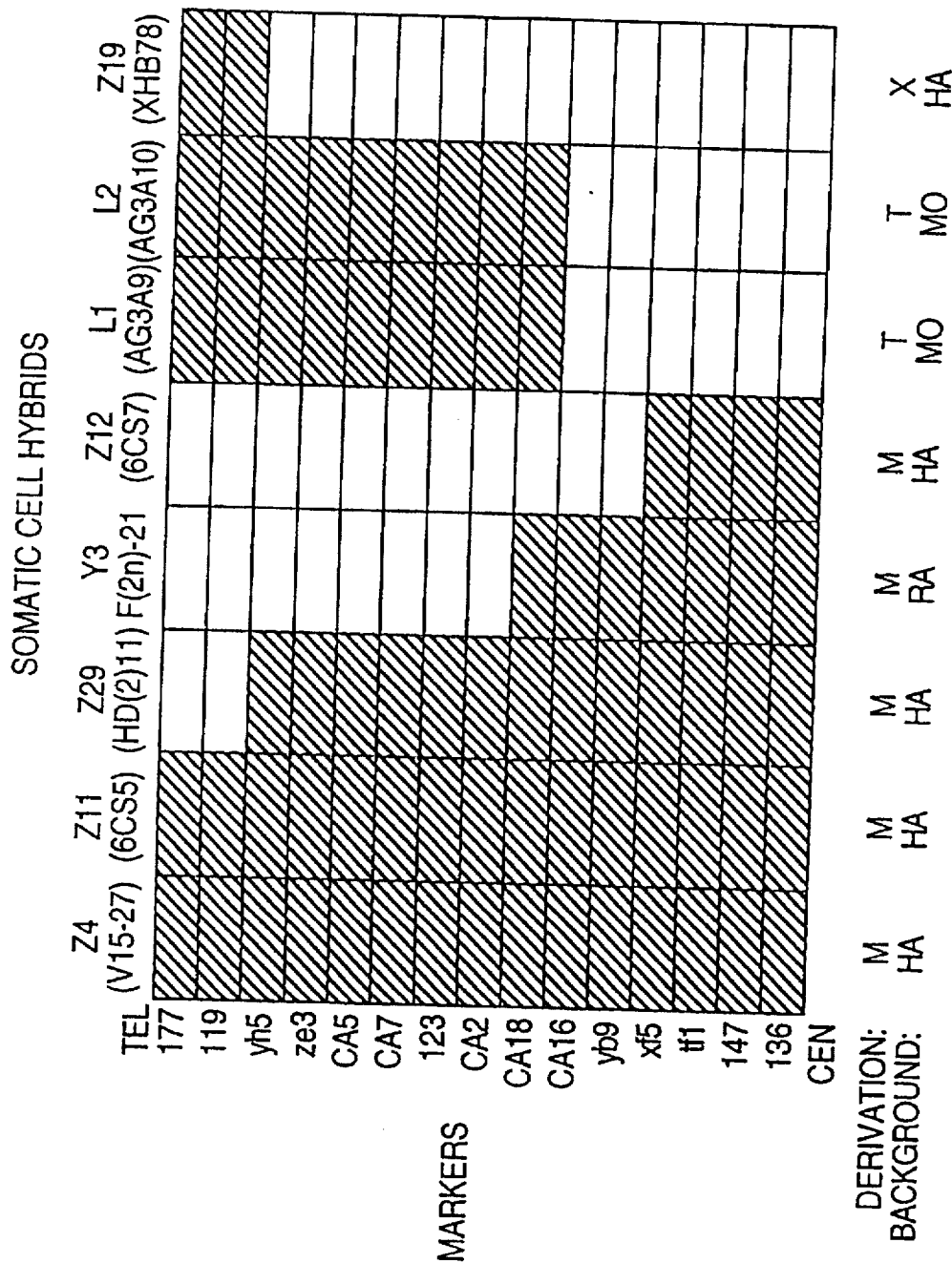
FIG. 1 summarizes the markers retained in somatic cell hybrids used in locating the hMSH2 gene.

A panel of human-hamster, human-mouse, and human-rat hybrid cell lines was developed to facilitate HNPCC mapping. Hybrids containing only portions of chromosome 2 were obtained by microcell-mediated chromosome transfer or by standard cell fusions following X-irradiation of the chromosome 2 donor. Additionally, two hybrids were used which contained a (X;2)(q28;p21) translocation derived from human fibroblasts. In previous studies, the HNPCC locus was mapped to the 25 cM region surrounding marker 123 and bordered by markers 119 and 136 (Peltomaki et al., 1993a). Thirty-eight hybrids were screened with these three chromosome 2p markers. Eight of the hybrids proved useful for mapping the relevant portion of chromosome 2p. For example, hybrids L1 and L2 contained the distal half of the region, including marker 123, while hybrid y3 contained the half proximal to marker 123 (FIG. 1).

Methods

Methods for the derivation of microcell-mediated chromosome 2 hybrids have been described previously (Chen et al., 1992; Spurr et al., 1993). Some hybrids were generated following fusion of X-irradiated donor cells containing human chromosome 2 to CHO cells (Chen et al., 1994). Mouse hybrids were derived by fusing FIPRT deficient L cells (A9) with human fibroblasts (GM7503) containing a t(X;2)(q28,p21) translocation and selecting in media containing HAT.

Example 2

Polymorphic Markers

To map more finely the HNPCC locus, additional polymorphic markers were obtained in three ways. First, a genomic clone containing 85 kb surrounding the 123 marker was used for fluorescence in situ hybridization (FISH) to localize it to chromosomal band 2p16.3 (FIG. 2A,B). The 2p16 band region was then microdissected; and the sequences within this band were amplified using the polymerase chain reaction and subcloned into plasmid vectors (see Experimental Procedures). The accuracy of the microdissection was confirmed using dual-color FISH by simultaneously hybridizing to microdissected material and a genomic clone containing marker 123 (FIG. 2C,D). The subclones were screened by hybridization to a $(CA)_{15}$ probe, and hybridizing clones identified and sequenced. These sequences were then used to design oligonucleotide primers for PCR analysis of genomic DNA. Nineteen $(CA)_n$ repeat markers were identified in this way. Of these, four were highly polymorphic and mapped to the region between markers 119 and 136, as assessed by the somatic cell hybrid panel exhibited in FIG. 1. Second, eight additional $(CA)_n$ markers, cloned randomly from human genomic DNA using a poly (CA) probe, were found to lie between markers 119 and 136 by linkage analysis in CEPH pedigrees. Five of these were particularly informative and were used in our subsequent studies. Finally, one additional marker was identified by screening subclones of a genomic P1 clone containing marker 123 with a $(CA)_{15}$ probe. Through these analyses, thirteen new polymorphic markers were identified in the 25 cM interval between markers 119 and 136, resulting in an average marker spacing of ~2 cM (Table II). These markers were mapped with respect to one another by linkage in CEPH and HNPCC pedigrees as well as by analysis of somatic cell hybrids. These two mapping techniques provided consistent and complementary information. For example, the relative positions of CA16 and CA18 could not be distinguished through linkage analysis but could be determined with the somatic cell hybrids L1, L2, and Y3. Conversely, the relative position of the ze3 and yh5 markers could not be determined through somatic cell hybrid mapping, but could be discerned by linkage analysis.

TABLE II

| MARKER | DERIVATION | CM | LOD | HETEROZYGOSITY | YAC CLONES | P1 CLONES |
|---|---|---|---|---|---|---|
| 177 (AFM267zc9) | T | — | | 0.84 | | |
| 119 (AFM077yb7) | T | 6.1 | 5.5 | 0.77 | 11E1 | 406 |
| yh5 (AFM337yh5) | T | 6.4 | 15.4 | 0.76 | 4F4, 1E1 | 838, 839, 840 |
| ze3 (AFM200ze3) | T | 0.0 | — | 0.61 | 4F4, 1E1, 9H6, 4A10 | 836, 837 |
| CA5 (CA5) | M | 2.1 | 4.7 | 0.77 | 7F10, 4E2, 5A11 | 820 |
| CA7 (CA7) | M | 1.7 | 3 | 0.78 | 6B8 | |
| 123 (AFM093xh3) | T | 2.4 | 9.9 | 0.76 | 3D11, 8C7 | 210, 211 |
| CA2 (CA2) | P | 0.0 | — | 0.75 | 3D11, 8C7 | 210, 211 |
| CA18 (CA18) | M | 4.3 | 17.1 | 0.71 | 8E5 | |
| CA16 (CA16) | M | 0.0 | — | 0.69 | 8E5 | |
| yb9 (AFM320yb9) | T | 1.1 | 3.9 | 0.80 | 264 | |
| xf5 AFM310xf5) | T | 2.7 | 17.6 | 0.76 | | |

TABLE II-continued

| MARKER | DERIVATION | CM | LOD | HETEROZYGOSITY | YAC CLONES | P1 CLONES |
|---|---|---|---|---|---|---|
| xf1 (AFM348tf1) | T | 0.0 | — | 0.79 | | |
| 147 (AFM199vb6) | T | 2.6 | 9.8 | 0.73 | | |
| 136 (AFM172xe7) | T | 2 | | 0.73 | | |
| 134 (AFM168xg11) | T | 1 | | 0.76 | | 387, 388, 389 |

Methods

All markers were obtained by screening human genomic libraries with radiolabelled $(CA)_n$ probes (Weber and May, 1989). The "T" markers (see Table 1) were generated from a library made from total human genomic DNA, as described in Weissenbach et al., 1992. The "M" markers were made from libraries generated from microdissected chromosome 2p16, as described below. The CA2 marker was generated from a library made from P1 clone 210 digested to completion with Sau3 and cloned into the XhoI site of lambda YES (Elledge et al., 1991). The sequences of the clones obtained from these libraries were determined, and primers surrounding the CA repeats chosen. Only primers giving robust amplification and high heterozygosity were used for detailed analysis of HNPCC kindreds. All markers used in this study were shown to be derived from chromosome 2p by both linkage analysis in the CEPH pedigrees and evaluation in the somatic cell hybrid panel shown in FIG. 1. The sequences of the primers and other details specific for each marker have been deposited with the Genome Data Base. Linkage analyses to obtain the map of the marker loci in CEPH families 1331, 1332, 1347, 1362, 1413, 1416, 884, and 102 (Weissenbach et al., 1992) were performed using the CLINK program of the LINKAGE program package (Lathrop et al., 1984) with the no sex difference option and 11-point computations. The odds for the best locus order supported by the data were evaluated against pairwise inversions of the loci.

Example 3

Genomic Clones

Many of the polymorphic markers shown in Table 1 were used to derive genomic clones containing 2p16 sequences. Genomic clones were obtained by PCR screening of human Pt and YAC libraries with these polymorphic markers, with ten additional sequence tagged sites (STS) derived from chromosome 2p16 microdissection, or with YAC junctions. Twenty-three P1 clones, each containing 85–95 kb, were obtained, as well as 35 YAC clones, containing 300 to 1800 kb. The YAC clones in some cases confirmed the linkage and somatic cell hybrid maps. For example, markers ze3 and yh5 were both found in YAC's 4F4 and 1E1 while CA16 and CA18 were both found in YAC 8E5, documenting their proximity. The highest density of genomic clones (28 YAC and 17 P 1 clones) was obtained between markers yb9 and yh5 (Table 1), which became the region most likely to contain the HNPCC gene during the course of these studies. The region between yh5 and yb9 was predicted to contain ~9 Mb (assuming 1 Mb/per cM). Based on the sizes of the YAC clones, and taking into account their chimerism, we estimated that they contained over 70% of the sequences between yh5 and yb9.

Methods

The markers described in Table 1 were used to screen YAC or P1 libraries by PCR. The CEPH A library was obtained from Research Genetics, Inc. and consisted of 21,000 YAC clones, arrayed in a format allowing facile screening and unambiguous identification of positive clones. The sizes of ten of the YAC clones containing markers were determined by transverse alternating pulse-field gel electrophoresis using a GeneLine II apparatus from Beckman and found to average 0.7 Mb (range 0.2–1.8 Mb). In some cases, inverse PCR was used to determine the YAC junctions (Joslyn et al., 1991), and the derived sequence used for "chromosome walking" with the YAC or P1 libraries. The junctions were also used to design primers to test whether the ends of the YAC clones could be localized to chromosome 2p16 (and therefore presumably be non-chimeric). Three of four YAC clones which were tested in this way had both ends within the expected region of chromosome 2, as judged by analysis with the somatic cell hybrid panel. The human genomic P1 library was also screened by PCR (Genome Systems, Inc.). P1 clones M1015 and M1016, containing the hMSH2 gene, were used to determine intron-exon borders using sequencing primers from the exons and SequiTherm™ polymerase (Epicentre Technologies).

Example 4

Analysis of HNPCC Families

The markers described in Table 1 were then used to analyze six large HNPCC kindreds previously linked to chromosome 2p (Peltomaki et al., 1993a). Two hundred thirteen individuals, including 56 members affected with colorectal or endometrial cancer, were examined. Four of the kindreds were from the United States, one from Newfoundland and one from New Zealand. To increase the number of affected individuals that could be examined, we obtained formalin-fixed, paraffin-embedded sections of normal tissues from deceased individuals and purified DNA from them (Goelz et al., 1985a). A single allele of each of the thirteen markers was found to segregate with disease in each of the six families (i.e., the allele was found in over 50% of affected individuals). No allele of any marker was shared among the affected members of more than three kindreds.

Fourteen of the affected members contained only a subset of the expected alleles and therefore had undergone recombination between markers 119 and 136. Eleven of these individuals appeared to have simple, single recombination events. The most informative of these was in individual 148 from the J kindred and individual 44 from kindred 62 1 (FIG. 3). Individual 621–44 apparently retained the disease linked allele at markers distal to CA5, while demonstrating multiple recombinants at more proximal loci, thus placing the CA5 marker at the proximal border of the HNPCC locus. Individual J-148 apparently retained the disease-linked allele at all markers proximal to yh5, while exhibiting recombinants at yh5 and 119, thus placing the distal border at yh5. Assuming that the same gene was involved in both the J and 62 1 kindreds, the HNPCC gene was predicted to reside between markers CA5 and yh5, an area spanning approximately 2 cM (Table 1).

The DNA of three affected individuals (C-202, 4-156, 4-92) appeared to have undergone two recombinations in the area. There was probably one recombinant per generation, and this could be demonstrated in C-202 by analysis of DNA from his parents; in the other cases, parental DNA was not available. All three individuals retained disease-linked alleles at CA5 and ze3 but not at more proximal and distal loci (FIG. 3). Combined with the data from the patients with single recombinations, the double recombinants suggested that the HNPCC gene resided between CA5 and ze3, a distance spanning less than 2 cM.

To determine the physical distances separating CA5, ze3, and yh5, metaphase and interphase FISH analysis was carried out. Dual-color FISH with P1 clones containing these markers was performed with P1 clones 820 and 838 (containing the markers CA5 and yh5, respectively) labeled with biotin and detected with fluorescein-labelled avidin, and clone 836 (containing marker ze3) labelled with Spectrum-Orange (Meltzer et al., 1992). The hybridization signals of these markers appeared coincident on metaphase chromosomes, confirming that they resided within an interval of <1.0 Mb. When FISH was performed on interphase nuclei, the relative positions of the three markers could be determined and the distances between them estimated (Trask et al., 1989). The results confirmed that the orientation of the markers was telomere-yh5-ze3-CA5-centromere (data not shown). Direct measurement of the distance between yh5 and ze3 was estimated at <0.3 Mb, consistent with the presence of both of these markers on YAC clones 4E4 and 1E1. Measurements of 48 interphase chromosomes provided an estimate of the distance between ze3 and CA5 at <0.8 Mb, independently confirming the linkage data.

Methods

G-banded metaphase chromosomes were microdissected with glass microneedles and amplified by PCR as previously described (Guan et al., 1993 Kao and Yu, 1991). For dual-color FISH, the PCR product was fluorochrome labelled (Spectrum-Orange, Imageneries, Naperville, Ill.) or biotinylated in a secondary PCR reaction. P1 clones were labelled by nick-translation or by degenerate oligonucleotide primers (Guan et al., 1993). FISH was carried out as previously described (Guan et al., 1993) and visualized with a Zeiss Axiophot equipped with a dual-bandpass filter. For analysis of interphase FISH patterns, the distance between hybridization signals was measured in a minimum of 24 nuclei (Trask et al., 1989).

Example 5

Candidate Genes

On the basis of the mapping results described above, we could determine whether a given gene was a candidate for HNPCC by determining its position relative to the CA5-ze3 domain. The first gene considered was a human homolog of the Drosophila SOS gene (reviewed by Egan and Weinberg, 1993). This gene transmits signals from membrane bound receptors to the ras pathway in diverse eukaryotes. It was considered a candidate because another ras-interacting gene, NF1, causes a cancer predisposition syndrome (Viskochil et al., 1990; Wallace et al., 1990), and SOS has been localized to chromosome 2p16-21 by in situ hybridization (Webb et al., 1993). Using PCR to amplify SOS sequences from the hybrid panel, however, SOS was found to be distal to the CA5-yh5 domain (present in hybrid Z19 but not Z29).

We next examined the interferon-inducible RNA activated protein kinase gene PKR. This gene has been shown to have tumor suppressor ability (reviewed by Lengyel, 1993) and to map close to 2p16 (Hanash et al., 1993). We could not initially exclude PKR from the HNPCC domain, and therefore determined the sequence of its coding region in two individuals from HNPCC kindred C. Reverse transcriptase was used to generate cDNA from lymphoblastoid derived RNA of these two individuals, and PCR performed with primers specific for PKR. The PKR products were sequenced, and no deviations from the published sequence was identified within the coding region (Meurs et al., 1990). Subsequent studies showed that the PKR gene was distal to the yh5 marker, and thus could be excluded as a basis for HNPCC.

We then considered human homologs of the MutL and MutS mismatch repair genes previously shown to produce microsatellite instability in bacteria and yeast when disrupted (Levinson and Gutman, 1987; Strand et al., 1993). A human homolog of the yeast MutL-related gene PMS1 (Kramer et al., 1989) does not appear to reside on chromosome 2p (M. Liskay, personal communication). To identify homologs of MutS, we used degenerate oligonucleotide primers to PCR-amplify cDNA from colon cancer cell lines. The same primers had been previously used to identify the yeast MSH2 gene on the basis of its MutS homology (Reenan and Kolodner, 1992). Under non-stringent conditions of PCR, a fragment of the expected size was obtained and these fragments were cloned into plasmid vectors. Most of the clones contained ribosomal RNA genes, representing abundant transcripts with weak homology to the degenerate primers. A subset of the clones, however, contained sequences similar to that of the yeast MSH2 gene, and one such clone, pNP-23, was evaluated further. The human gene from which this clone is derived is hereafter referred to as hMSH2.

The insert from clone pNP-23 was used as a probe in Southern blots of somatic cell hybrid DNA. This insert hybridized to one or two fragments in human genomic DNA digested with PstI or EcoRI, respectively, and these fragments were present in hybrid Z30, containing most of human chromosome 2p. Analysis of other hybrids showed that the fragment was present in hybrids Z11, Z29, L1 and L2, but not Z12, Y3 or Z19, thereby localizing the human MSH2 (hMSH2) gene to a region bordered by markers CA18 and 119 (examples in FIG. 4). The YAC clones listed in Table 1 were then analyzed, and EcoRI and PstI fragments of the expected size identified in YAC 5A11, derived from screening the YAC library with the CA5 marker (FIG. 4).

To confirm the Southern blots, we designed non-degenerate primers on the basis of the sequence of pNP-23. Several sets of primers were tested so that genomic DNA could be used as a template for PCR; an intervening intron prevented the original primers from being used effectively with templates other than cDNA. PCR with these primers was perfectly consistent with the Southern blot results. The expected 101 bp fragment was present in hybrids Z4, Z11; Z29, L1, and L2, and in YAC 5A11, but not in other hybrids or YAC clones (not shown).

The localization of hMSH2 sequences to YAC 5All demonstrated the proximity of these sequences to marker CA5. To determine the distance and relative orientation of hMSH2 with respect to CA5, we performed interphase FISH analysis. P1 clones containing CA5, ze3 and hMSH2 sequences (clones 820, 836, and M1015, respectively) were simultaneously hybridized to interphase nuclei following fluorescein and Spectrum Orange labelling (Meltzer et al., 1992). The results demonstrated that MSH2 resides within the HNPCC locus defined by linkage analysis to lie between CA5 and ze3, and less than 0.3 Mb from marker CA5 (FIG. 2E).

cDNA libraries generated from human colon cancer cells or from human fetal brain tissues were then screened with the insert of pNP-23 to obtain additional sequences from this gene. Seventy-five cDNA clones were initially identified and partially sequenced. PCR products representing the ends of the cDNA sequence contig were then used as probes to re-screen the cDNA libraries. This cDNA "walk" was repeated again with the new contig ends. Altogether, 147 cDNA clones were identified. The composite sequence derived from these clones is shown in FIG. 5. An open reading frame (ORF) began 69 nt downstream of the 5' end of the cDNA contig, and continued for 2802 bp. The methionine initiating this ORF was in a sequence context compatible with efficient translation (Kozak, 1986) and was preceded by in-frame termination codons. RNA from placenta and brain were used in a PCR-based procedure (RACE, Frohman et al., 1988) to independently determine the position of the 5' end of hMSH2 transcripts. This analysis demonstrated that the 5' ends of all detectable transcripts were less than 100 bp upstream of the sequence shown in FIG. 5, and were heterogeneous upstream of nt -69. The region of highest homology to the yeast MSH2 gene is shown in FIG. 6. This region encompassed the helix-turn-helix domain perhaps responsible for MutS binding to DNA (Reenan and Kolodner, 1992). The yeast and human MSH2 proteins were 77% identical between codons 615 and 788. There were several other blocks of similar amino acids distributed throughout the length of these two proteins (966 and 934 amino acids in yeast and human, respectively).

Methods cDNA generated from the RNA of colorectal cancer cells with reverse transcriptase was used as template for PCR with the degenerate primers-5'-CTG GAT CCA C(G/A/T/C) G G(G/A/T/C)C C(G/A/T/C)A A(T/C)A TG-3' and 5'-CTG GAT CC(G/A) TA(G/A) TG(G/AFF/C) GT (G/A/T/C) (G/A)C(G/A) AA-3'. These two primers were used previously to identify the yeast MSH2 gene and were based on sequences conserved among related mammalian and bacterial genes (Reenan and Kolodner, 1992). The optimal PCR conditions for detecting the human MSH2 gene consisted of 35 cycles at 95° for 30 seconds, 41° for 90 seconds, and 70° for 90 seconds, in the buffer described previously (Sidransky et al., 1991). PCR products were cloned into T-tailed vectors as described (Holton and Graham, 1991) and sequenced with modified T7 polymerase (USB). The insert from one clone (pNP-23) containing human sequences homologous to the yeast MSH2 gene was then used to screen cDNA libraries generated from RNA of SW480 colon cancer cells (Clontech) or of fetal brain (Stratagene). After two further rounds of screening, positive clones were converted into plasmids and sequenced using modified T7 polymerase (Kinzler et al., 1991). In some cases, the inserts were amplified using one hMSH2-specific primer and one vector-specific primer, and then sequenced with SequiTherm Polymerase (Epicentre Technologies). To determine the 5' end of MSH2 transcripts, RACE was performed (Frohman et al., 1989) using brain and placenta cDNA (Clontech).

Example 6

Mutations of hMSH2

The physical mapping of hMSH2 to the HNPCC locus was intriguing but could not prove that this gene was responsible for the disease. To obtain more compelling evidence, we determined whether germ line mutations of hMSH2 were present in the two HNPCC kindreds that originally established linkage to chromosome 2 (Peltomaid et al., 1993a). Intron-exon borders within the most conserved region of hMSH2 (FIG. 6) were determined by sequencing genomic PCR fragments containing adjacent exons. Genomic DNA samples from the lymphocytes of affected members of these two kindreds were then used as templates for PCR to determine the sequence of this domain. The DNA from individual J42, afflicted with colon and endometrial cancer at ages 42 and 44, respectively, was found to contain one allele with a C to T transition at codon 622 (CCA to CTA), resulting in a substitution of leucine for proline (FIG. 7, top). Twenty additional DNA samples from unrelated individuals all encoded proline at this position. Twenty one members of the J kindred were then analyzed by direct sequencing of PCR products. All eleven affected individuals contained one allele with a C to T transition in codon 622, while all ten unaffected members contained two normal alleles, thus documenting perfect segregation with disease. Importantly, this proline was at a highly conserved position, the identical residue being found in all known MutS related genes from prokaryotes and eukaryotes (FIG. 6 and Reenan and Kolodner, 1992).

No mutations of the conserved region of MSH2 were identified in kindred C, so we next examined other pans of the hMSH2 transcript. RNA was purified from lymphoblastoid cells of patient C-202, a 27 year old male with colon cancer. Reverse transcriptase coupled PCR (RT-PCR) was used to generate four hMSH2-specific products encompassing codons 89 to 934 from this RNA (see Experimental Procedures). An abnormal, smaller RT-PCR product was identified with one of the primer pairs used. Mapping and sequencing studies using various MSH2 primers showed that the abnormal product was the result of a presumptive splicing defect which removed codons 265 to 314 from the hMSH2 transcript. The abnormal transcript was found to segregate with disease in the C kindred, and was not found in twenty unrelated individuals.

We next wished to determine whether hMSH2 was altered in one of the more recently linked families (R.P. and M.N-L., unpublished data), and chose kindred 8 for detailed analysis. DNA and RNA were obtained from lymphoblastoid cells of 8-143, a 42 year old male with colon cancer. The conserved region of hMSH2 was amplified from genomic DNA using PCR and directly sequenced. A T to C substitution was noted in the polypyrimidine tract upstream of the exon beginning at codon 669 (at intron position −6). However, this substitution was also found in two of twenty unrelated, normal individuals, and was therefore a polymorphism unrelated to the disease, with an allele frequency of 0.05. Most of the hMSH2 coding region was then amplified by RT-PCR, as described above, and no abnormal transcripts were detected. Sequencing of the PCR products, however, revealed a C to T transition at codon 406 (CGA to TGA) causing substitution of a termination codon for an arginine residue. RNA was available from the lymphocytes of a second affected member of kindred 8, and the same stop codon was identified. This alteration was not found in twenty other, unrelated individuals.

Finally, we wished to determine whether mutations of this gene occurred in RER[+] tumors from patients without evident family histories of cancer. The conserved region of MSH2 was studied in four colorectal tumor cell lines from such patients using genomic DNA as templates for PCR. One tumor (from patient Cx10) was found to contain two hMSH2 alterations. The first was a C to T transition in codon 639 (CAT to TAT), resulting in a substitution of tyrosine for histidine. This change was not found in any of twenty samples from unrelated individuals, but was present in the DNA from normal colon of this patient, and was therefore likely to represent a germ line change (FIG. 7, middle). Like the missense mutation in the J kindred, the Cx10 alteration was at a position perfectly conserved in all MutS homologs (FIG. 6 and Reenan and Kolodner, 1992). The second alteration in the tumor from Cx10 was a substitution of a GT dinucleotide for an A in codon 663 (ATG to TGTG). The resultant one bp insertion was predicted to cause a frameshift, producing a termination codon 36 nt downstream. This mutation was demonstrated in both RNA and DNA purified from the Cx10 tumor, but was not present in the patient's normal colon, so represented a somatic mutation (FIG. 7, bottom). The PCR products from Cx10 were cloned and sequenced, and the insertion mutation at codon 663 and the transition at codon 639 were shown to reside on different alleles.

Methods

To detect mutations, PCR products were generated from cDNA and human genomic DNA templates, then sequenced directly using SequiTherm™. In some cases, the PCR products were cloned into T-tailed vectors for sequencing to confirm the direct sequencing data. The primers used to amplify the conserved region of MSH2 from genomic DNA were 5'-CCA CAA TGG ACA CTT CTG C-3' and 5'-CAC CTG TTC CAT ATG TAC G-3', resulting in a 1.4 kb fragment containing hMSH2 codons 614 to 705, and primers 5'-AAA ATG GGT TGC AAA CAT GC-3' and 5'-GTG ATA GTA CTC ATG GCC C-3', resulting in a 2.0 kb fragment containing MSH2 cDNA codons 683 to 783. Primers for RT-PCR were 5'-AGA TCT TCT TCT GGT TCG TC-3' and 5'-GCC AAC AAT AAT TTC TGG TG-3' for codons 89 to 433, 5'-TGG ATA AGA ACA GAA TAG AGG-3' and 5'-CCA CAA TGG ACA CTT CTG C-3' for codons 350–705, 5'-CAC CTG TTC CAT ATG TAC G-3' and 5'-AAA ATG GGT TGC AAA CAT GC-3' for codons 614 to 783, and 5'-GTG ATA GTA CTC ATG GCC C-3' and 5'-GAC AAT AGC TTA TCA ATA TTA CC-3' for codons 683–949.

Discussion

Three major conclusions can be drawn from the examples described here. First, physical mapping and linkage analysis localized the HNPCC locus on chromosome 2 to an 0.8 Mb segment bordered by markers CA5 and ze3. Second, a new human homolog of the yeast MSH2 gene was identified, and this gene shown to lie in the same 0.8 Mb interval. Third, alterations of the hMSH2 gene occurred in the germ line of patients with RER+ tumors, with or without classical HNPCC, and additional somatic alterations of this gene occurred in tumors (Summarized in Table I). The alterations were at highly conserved regions or significantly altered the expected gene product and thus represent mutations with important functional effects. These results indicate that mutations of hMSH2 are responsible for HNPCC and the RER+ positive phenotype found in tumors.

These data have substantial implications for understanding the neoplastic disease observed in HNPCC. In particular, they suggest that the microsatellite alterations previously observed in tumors from these patients are not epiphenomena, but are intrinsically related to pathogenesis. Additionally, the mutations observed in yeast and bacteria with defective MutS-related genes are not confined to insertions and deletions at simple repeated sequences, though these sequences provide convenient tools for analysis (Modrich, 1991). Similarly, one would expect that many mutations, in addition to microsatellite insertions or deletions, would be found in HNPCC tumors. This could lead to the multiple, sequential mutations in oncogenes and tumor suppressor genes which have been shown to drive colorectal tumorigenesis (Fearon and Vogelstein, 1990).

Thus, the molecular pathogenesis of HNPCC tumors is likely to be similar to that occurring in non-HNPCC cases, though accelerated by the increased rate of mutation associated with mismatch repair defects. Accordingly, colon tumors from HNPCC patients have been shown to contain mutations of APC, p53 and RAS at frequencies similar to those found in sporadic colorectal cancers (Aaltonen et al., 1993).

Colorectal tumors from HNPCC patients are distinguished by their relatively normal cytogenetic composition (Kouri et al., 1990), and sporadic, RER+ tumors have been demonstrated to have substantially fewer chromosome losses than those occurring in RER+ cases (Thibodeau et al., 1993; Aaltonen et al., 1993). These data suggest that genetic heterogeneity is critical for colorectal cancer development, but can be generated in two different ways (Thibodeau et al., 1993). Most commonly, it develops through gross alterations resulting in aneuploidy, as suggested nearly eighty years ago (Boveri, 1914). In HNPCC-derived tumors and RER+ sporadic tumors, the diversity is presumably more subtle, consisting of multiple small sequence changes distributed throughout the genome. The latter mechanism of generating diversity may be less dangerous to the host, as HNPCC patients, as well as patients with RER+ sporadic tumors, appear to have a better prognosis than would be expected from histopathologic analysis of their tumors (Ionov et al..; 1993; Thibodeau et al., 1993; Lethe et al., 1993; Lynch et al., 1993).

References

Aaltonen, L. A., Peltomaki, P., Leach, F. S., Sistonen, P., Pylkkanen, L., Mecklin, J-P., Jarvinen, H., Powell, S. M., Jen, J., Hamilton, S. R., Petersen, G. M., Kinzler, K. W., Vogelstein, B., and de la Chapelle, A. (1993). Clues to the pathogenesis of familial colorectal cancer. Science 260, 812–816.

Baylin, S. B., Makes, M., Wu, J., C-Y, R-W., de Bustres, A., Vertino, P., and Nelkin, B. D. (1991). Abnormal patterns of DNA methylation in human neoplasia: Potential consequences for tumor progression. Cancer Cells 3, 383, 390.

Boveri, T. (1914). Zur Frage der Entstehung maligner tumoren. Gustave Fischer Verlag, Jena, Vol. 1.

Chen, D. J., Park, M. S., Campbell, E., Oshimura, M., Liu, P., Zhao, Y., Whim, B. F., and Siciliano, M. J. (1992). Assignment of a human DNA double-strand break repair gene (XRCC5) to chromosome 2. Genomics 13, 1088–1094.

Chen, D. J., Marrone, B., Nguyen, T., Stackhouse, M., Zhao, Y., and Sicilano, J. J., (1994). Regional assignment of a human radiation repair gene (XRCC5) to 2q35 by X-ray hybrid mapping. Genomics, in press.

Egan, S. E., and Weinberg, R. A. (1993). The pathway to signal achievement. Nature 365, 781–783.

Elledge, S. J., Mulligan, J. T., Ramer, S. W., Spottswood, M., and Davis R. W. (1991). Lambda YES: a multifunctional cDNA expression vector for the isolation of genes by complementation of yeast and Escherichia coli mutations. Proc. Natl. Acad. Sci. USA 88, 1731–1735.

Fang, W.-h. and P. Modrieh (1993). Human strand-specific mismatch repair occurs by a bidirectional mechanism similar to that of the bacterial reaction. J. Biol. Chem. 268, 11838–11844.

Fearon, E. R., and Vogelstein, B. (1990). A genetic model for colorectal tumorigenesis. Cell 61,759–767.

Frohman, M. A, Dush, M. K., and Martin, G. R. (1988). Rapid production of full-length cDNAs from rare transcripts: Amplification using a single gene-specific oligonucleotide primer. Proc. Natl. Acad. Sci. USA 85, 8998–9002.

Goelz, S. E., Hamilton, S. R., and Vogelstein, B. Purification of DNA from Formaldehyde Fixed and Paraffin Embedded Human Tissue. (1985a). Biochem. Biophys. Res. Commun. 130, 118–126.

Goelz, S. E., Vogelstein, B., Hamilton, S. R., and Feinberg, A. P. Hypomethyhtion of DNA from Benign and Malignant Human Colon Neoplasms. (1985b). Science 228, 187–190.

Guan, X.-Y., Trent, J. M., and Meltzer, P. S. (1993). Generation of band-specific painting probes from a single microdissected chromosome. Human Molecular Genetics 2, 1117–1121.

Han, H-J., Yanagisawa, A., Kato, Y., Park, J-G., and Nakamura, Y. (1993). Genetic instability in pancreatic cancer and poorly differentiated type of gastric cancer. Cancer Research 53, 5087–5089.

Hanash, S. M., Beretta, L., Barcroft, C. L., Sheldon, S., Glover, T. W., Ungar, D., and Sonenberg, N. (1993). Mapping of the gene for interferon-inducible dsRNA-dependent protein kinase to chromosome region 2p21-22: A site of rearrangements in myeloproliferative disorders. Genes, Chromosomes & Cancer 8, 34–37.

Holmes, J., S. Clark and P. Modrich (1990). Strand-specific mimsatch correction in nuclear extracts of human and *Drosophila melanogaster* cell lines. Proc. Natl. Acad. Sci. U.S.A. 87, 5837–5841.

Holton, T. A., and Graham, M. W. (1991). A simple and efficient method for direct cloning of PCR products using ddT-tailed vectors. Nucleic Acids Research 19, 1156.

Ionov, Y. M., Peinado, A., Malkhosyan, S., Shibata, D., and Perucho M. (1993). Ubiquitous somatic mutations in simple repeated sequences reveal a new mechanism for colonic carcinogenesis. Nature 363, 558–561.

Jass, J. R., Stewart, S. M. (1992). Evolution of hereditary non-polyposis colorectal cancer. Gut 33, 783–786.

Joslyn, G., Carlson, M., Thilveris, A., Albertsen, H., Gelben, L., Samowitz, W., Groden, J., Stevens, J., Spirio, L., Robertson, M., Sargeant, L., Krapcho, K., Wolff, E., Butt, R., Hughes, J. P., Warrington, J., McPherson, J., Wasmuth, J., Le Paslier, D., Abderrahim, H., Cohen, D., Leppert, M., and White, R. (1991). Identification of deletion mutations and three new genes at the familial polyposis locus. Cell 66, 601–613.

Kao, F-T., and Yu, J-W. (1991). Chromosome microdissection and cloning in human genome and genetic disease analysis. Proc. Natl. Acad. Sci. USA 88, 1844–1848.

Kinzler, K. W., Nilbert, M. C., Su, L.-K., Vogelstein, B., Bryan, T. M., Levy, D. B., Smith, K. J., Preisinger, A. C., Hedge, P., McKechnie, D., Finniear, R., Markham, A., Groffen, J., Boguski, M. S., Altschul, S. F., Horii, A., Ando, H., Miyoshi, Y., Mild, Y., Nisbisho, I., Nakamura, Y. Identification of FAP Locus Genes from Chromosome 5q21. (1991). Science 253, 661–665.

Kouri, M., Laasonen, A., Mecklin, J. P., Jarvinen, H., Franssila, K., Pyrhonen, S. (1990). Diploid predominance in hereditary nonpolyposis colorectal carcinoma evaluated by flow cytometry. Cancer 65, 1825–1829.

Kozak, M. (1986). Point mutations define a sequence flanking the AUG initiator codon that modulates translation by Eukaryotic Ribosomes. Cell 44, 283–292.

Kramer, W., Kramer, B., Williamson, M. S., Fogel, S. (1989). Cloning and nucleotide sequence of DNA mismatch repair gene PMSI from *Saccharomyces cerevisiae*: homology of PMS1 to procaryotic MutL and HexB. Journal of Bacteriology 171, 5339–5346.

Knudson, A. G. (1993). All in the (cancer) family. Nature Genetics 5, 103–104.

Kunkel, T. A. (1993). Slippery DNA and diseases. Nature 365, 207–208.

Lathrop, G. M., Lalouel, J. M., Julier, C., and Ott, J. (1984). Strategies for multilocus linkage analysis in humans. Proc. Natl. Acad. Sci. USA 81, 3443–3446.

Lengyel, P. (1993). Tumor-suppressor genes: News about the interferon connection. Proc. Natl. Acad. Sci. USA 90, 5893–5895.

Levinson, G., and Gutman, G. A. (1987). High frequencies of short frameshifts in poly-CA/TG tandem repeats borne by bacteriophage M13 in *Escherichia coli* K-12. Nueleic Acids Research 15, 5323–5338.

Lindblom, A., Tannergard, P., Werelius, B., and Nordenskjold, .M. (1993). Genetic mapping of a second locus predisposing to hereditary non-polyposis colon cancer. Nature Genetics 5, 279–282.

Lothe, R. A., Peltomaki, P., Meling, G-L, Aaltonen, L. A., Nystrom-Lahti, M., Pylkkanen, L., Heimdal, K., Andersen, T. I., Moller, P., Rognum, T. O., Fossa, S. D., Haldorsen, T., Langmark, F., Bragger, A., de la Chapolle, A., and Barresea, A-L. (1993). Genomic instability in colorectal caner: Relationship to clinicopathological variables and family history. Cancer Research, in press.

Lynch, H. T., Omaha, M. W., Shaw, M. D. (1966). Hereditary factors in cancer. Arch Intern Med 117, 206–212.

Lynch, H. T., Smyrk, T. C., Watson, P., Lanspa, S. J., Lynch, J. F., Lynch, P. M., Cavalieri, R. J., and Boland, C. R. (1993). Genetics, natural history, tumor spectrum, and pathology of hereditary nonpolyposis colorectal cancer: An updated review. Gastroenterology 104, 1535–1549.

Meltzer, P. S., Guan, X-Y., Burgess, A., and Trent, J. M. (1992). Rapid generation of region specific probes by chromosome microdissection and their application. Nature Genetics 1, 24–28.

Meurs, E., Chong, K., Galabru, J., Thomas, N. S. B., Kerr, I. M., Williams, B. R. G., and Hovanessian, A. G. (1990). Molecular cloning and characterization of the human double-stranded RNA-activated protein kinase induced by interferon. Cell 62, 379–390.

Modrich, P. (1991). Mechanisms and biological effects of mismatch repair. Ann. Rev. Genet. 25, 229–253.

Peinado, M. A., Malkhosyan, S., Velazquez, A., and Perucho, M. (1992). Isolation and characterization of allelic losses and gains in colorectal tumors by arbitrarily primed polymerase chain reaction. Proc. Natl. Acad. Sci. USA 89, 10065–10069.

Peltomaki, P., Aaltonen, L. A., Sistonen, P., Pylkkanen, L., Mecklin, J-P., Jarvinen, H., Green, J. S., Jass, J. R., Weber, J. L., Leach, F. S., Petersen, G. M., Hamilton, S. R., de la Chapelle, A., and Vogelstein, B. (1993a). Genetic mapping of a locus predisposing to human colorectal cancer. Science 260, 810–812.

Pukkila, P. J., Petscon, I., Herman, G., Modrich, P., and Meselson, M. (1983). Effects of high levels of DNA adeninc methylation on methyl-directed mismatch repair in *Escherichia coli*. Genetics 104, 571–582.

Reenan, R. A., Kolodner, R. D. (1992). Isolation and characterization of two *Saccharomyces cerevisiae* genes encoding homologs of the bacterial HexA and MutS mismatch repair proteins. Genetics 132, 963–973.

Risinger, J. I., Berchuck, A., Kohler, M. F., Watson, P., Lynch, H. T., and Boyd, J. (1993). Genetic instability of microsatellites in endometrial carcinoma. Cancer Research 53, 5100–5103.

Sidransky, D., von Eschenbach, A., Tsai, Y. C., Jones, P., Summerhayes, I., Marshall, F., Paul, M., Green, P., Hamilton, S. R., Frost, P., Vogelstein, B. (1991). Identification of p53 Gene Mutations in Bladder Cancers and Urine Samples. Science 252, 706–709.

Spurr, N. K., Cox, S., Naylor, S. (1993). Report and abstracts of the Second International Workshop on human chromosome 2 mapping. Cytogenetics & Cell Genetics 64, 69–92.

Stanbridge, E. J. (1990). Human tumor suppressor genes. Ann. Rev. Genes 24, 615–657.

Strand, M., Prolla, T. A., Liskay, R. M., and Petes, T. D. (1993). Destabilization of tracts of simple repetitive DNA in yeast by mutations affecting DNA mismatch repair. Nature 365, 274–276.

Thibodeau, S. N., Bren, G., and Schaid, D. (1993). Microsatellite instability in cancer of the proximal colon. Science 260, 816–819.

Thomas, D. C., J. D. Roberts and T. A. Kunkel (1991). Heteroduplex repair in extracts of human HeLa cells. J. Biol. Chem. 266, 3744–3751.

Trask, B., Pinkel, D., and van den Engh, G. (1989). The proximity of DNA sequences in interphase cell nuclei is correlated to genomic distance and permits ordering of cosmids spanning 250 kilbase pairs. Genomics 5, 710–717.

Viskochil, D., Buchberg, A. M., Xu, G., Cawthon, R., Stevens, J., Wolff, R. K., Culver, M., Carey, J. C., Copeland, N. G., Jenkins, N. A., White, R., and O'Connell, P. (1990). Deletions and a translocation interrupt a cloned gene at the neurofibromatosis type 1 locus. Cell 62, 187–192.

Vogelstein, B., Fearon, E. R., Hamilton, S. R., Preisinger, A. C., Willard, H. F., Michelson, A. M., Riggs, A. D., and Orkin, S. H. (1987). Clonal Analysis Using Recombinant DNA Probes from the X Chromosome. Cancer Research 47, 4806–4813.

Wallace, M. R., Marchuk, D. A., Andersen, L. B., Letcher, R., Odeh, H. M., Saulino, A. M., Fountain, J. W., Brereton, A., Nicholson, J., Mitchell, A. L., Brownstein, B. H., Collins, F. S. (1990). Type 1 neurofibromatosis gene: Identification of a large transcript disrupted in three NF1 patients. Science 249, 181–186.

Warthin, A. S. (1913). Heredity with reference to carcinoma: As shown by the study of the cases examined in the pathological laboratory of the University of Michigan, 1895–1913. Arch. Int. Med 12, 546–555.

Watson, P., and Lynch, H. T. (1993). Extracolonic cancer in hereditary nonpolyposis colorectal cancer. Cancer 71, 677–685.

Webb, G. C., Jenkins, N. A., Largaespada, D. A., Copeland, N. G., Fernandez, C. S., and Bowtell, D. D. L. (1993). Mammalian homologues of the Drosophila Son of sevenless gene map to murine chromosomes 17 and 12 and to human chromosomes 2 and 14, respectively. Genomics 18, 14–19.

Weber, J. L., May P. E. (1989). Abundant class of human DNA polymorphisms which can be typed using the polymerase chain reaction. American Journal of Human Genetics 44, 338–396.

Weissenbach, J., Gyapay, G., Dib, C., Vignal A., Morissette, J., Millasseau, P., Vaysseix, G., and Lathrop, M. (1992). A second-generation linkage map of the human genome. Nature 359, 794–801.

---

---

We claim:

1. A method of determining a predisposition to cancer comprising:

testing a body sample of a human to ascertain the presence of a mutation in a gene identified as hMSH2 (human analog of bacterial MutS and *Saccharomyces cerevisine* MSH2) which affects hMSH2 expression or hMSH2 protein function, the presence of such a mutation indicating a predisposition to cancer.

2. The method of claim 1 wherein the sample is DNA.

3. The method of claim 1 wherein the sample is RNA.

4. The method of claim 1 wherein the sample is isolated from prenatal or embryonic cells.

5. A method of determining a predisposition to cancer associated with Lynch's Syndrome, comprising:

testing a body sample of a human to ascertain the presence of a mutation in a gene identified as hMSH2 (human analog of bacterial MutS and *Saccharomyces cerevisiae* MSH2) which affects hMSH2 expression or hMSH2 protein function, the presence of such a mutation indicating a predisposition to a cancer associated with Lynch's Syndrome.

\* \* \* \* \*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 2947 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( x i ) SEQUENCE DESCRIPTION: SEQ ID NO:1:

```
GGCGGGAAAC AGCTTAGTGG GTGTGGGGTC GCGCATTTTC TTCAACCAGG AGGTGAGGAG       60

GTTTCGACAT GGCGGTGCAG CCGAAGGAGA CGCTGCAGTT GGAGAGCGCG GCCGAGGTCG      120

GCTTCGTGCG CTTCTTTCAG GGCATGCCGG AGAAGCCGAC CACCACAGTG CGCCTTTTCG      180

ACCGGGGCGA CTTCTATACG GCGCACGGCG AGGACGCGCT GCTGGCCGCC CGGGAGGTGT      240

TCAAGACCCA GGGGGTGATC AAGTACATGG GGCCGGCAGG AGCAAAGAAT CTGCAGAGTG      300

TTGTGCTTAG TAAAATGAAT TTTGAATCTT TTGTAAAAGA TCTTCTTCTG GTTCGTCAGT      360

ATAGAGTTGA AGTTTATAAG AATAGAGCTG GAAATAAGGC ATCCAAGGAG AATGATTGGT      420

ATTTGGCATA TAAGGCTTCT CCTGGCAATC TCTCTCAGTT TGAAGACATT CTCTTTGGTA      480

ACAATGATAT GTCAGCTTCC ATTGGTGTTG TGGGTGTTAA AATGTCCGCA GTTGATGGCC      540

AGAGACAGGT TGGAGTTGGG TATGTGGATT CCATACAGAG GAAACTAGGA CTGTGTGAAT      600

TCCCTGATAA TGATCAGTTC TCCAATCTTG AGGCTCTCCT CATCCAGATT GGACCAAAGG      660
```

```
AATGTGTTTT ACCCGGAGGA GAGACTGCTG GAGACATGGG GAAACTGAGA CAGATAATTC    720
AAAGAGGAGG AATTCTGATC ACAGAAAGAA AAAAAGCTGA CTTTTCCACA AAAGACATTT    780
ATCAGGACCT CAACCGGTTG TTGAAAGGCA AAAGGGAGA  GCAGATGAAT AGTGCTGTAT    840
TGCCAGAAAT GGAGAATCAG GTTGCAGTTT CATCACTGTC TGCGGTAATC AAGTTTTAG     900
AACTCTTATC AGATGATTCC AACTTTGGAC AGTTTGAACT GACTACTTTT GACTTCAGCC    960
AGTATATGAA ATTGGATATT GCAGCAGTCA GAGCCCTTAA CCTTTTCAG  GGTTCTGTTG   1020
AAGATACCAC TGGCTCTCAG TCTCTGGCTG CCTTGCTGAA TAAGTGTAAA ACCCCTCAAG   1080
GACAAAGACT TGTTAACCAG TGGATTAAGC AGCCTCTCAT GGATAAGAAC AGAATAGAGG   1140
AGAGATTGAA TTTAGTGGAA GCTTTTGTAG AAGATGCAGA ATTGAGGCAG ACTTTACAAG   1200
AAGATTTACT TCGTCGATTC CCAGATCTTA ACCGACTTGC CAAGAAGTTT CAAAGACAAG   1260
CAGCAAACTT ACAAGATTGT TACCGACTCT ATCAGGGTAT AAATCAACTA CCTAATGTTA   1320
TACAGGCTCT GGAAAAACAT GAAGGAAAAC ACCAGAAATT ATTGTTGGCA GTTTTGTGA    1380
CTCCTCTTAC TGATCTTCGT TCTGACTTCT CCAAGTTTCA GGAAATGATA GAAACAACTT   1440
TAGATATGGA TCAGGTGGAA AACCATGAAT TCCTTGTAAA ACCTTCATTT GATCCTAATC   1500
TCAGTGAATT AAGAGAAATA ATGAATGACT TGGAAAAGAA GATGCAGTCA ACATTAATAA   1560
GTGCAGCCAG AGATCTTGGC TTGGACCCTG GCAAACAGAT TAAACTGGAT TCCAGTGCAC   1620
AGTTTGGATA TTACTTTCGT GTAACCTGTA AGGAAGAAAA AGTCCTTCGT AACAATAAAA   1680
ACTTTAGTAC TGTAGATATC CAGAAGAATG GTGTTAAATT TACCAACAGC AAATTGACTT   1740
CTTTAAATGA AGAGTATACC AAAAATAAAA CAGAATATGA AGAAGCCCAG GATGCCATTG   1800
TTAAAGAAAT TGTCAATATT TCTTCAGGCT ATGTAGAACC AATGCAGACA CTCAATGATG   1860
TGTTAGCTCA GCTAGATGCT GTTGTCAGCT TGCTCACGT  GTCAAATGGA GCACCTGTTC   1920
CATATGTACG ACCAGCCATT TTGGAGAAAG GACAAGGAAG AATTATATTA AAAGCATCCA   1980
GGCATGCTTG TGTTGAAGTT CAAGATGAAA TTGCATTTAT TCCTAATGAC GTATACTTTG   2040
AAAAAGATAA ACAGATGTTC CACATCATTA CTGGCCCCAA TATGGGAGGT AAATCAACAT   2100
ATATTCGACA AACTGGGGTG ATAGTACTCA TGGCCCAAAT TGGGTGTTTT GTGCCATGTG   2160
AGTCAGCAGA AGTGTCCATT GTGGACTGCA TCTTAGCCCG AGTAGGGGCT GGTGACAGTC   2220
AATTGAAAGG AGTCTCCACG TTCATGGCTG AAATGTTGGA AACTGCTTCT ATCCTCAGGT   2280
CTGCAACCAA AGATTCATTA ATAATCATAG ATGAATTGGG AAGAGGAACT TCTACCTACG   2340
ATGGATTTGG GTTAGCATGG GCTATATCAG AATACATTGC AACAAAGATT GGTGCTTTTT   2400
GCATGTTTGC AACCCATTTT CATGAACTTA CTGCCTTGGC CAATCAGATA CCAACTGTTA   2460
ATAATCTACA TGTCACAGCA CTCACCACTG AAGAGACCTT AACTATGCTT TATCAGGTGA   2520
AGAAAGGTGT CTGTGATCAA AGTTTTGGGA TTCATGTTGC AGAGCTTGCT AATTTCCCTA   2580
AGCATGTAAT AGAGTGTGCT AAACAGAAAG CCCTGGAACT TGAGGAGTTT CAGTATATTG   2640
GAGAATCGCA AGGATATGAT ATCATGGAAC CAGCAGCAAA GAAGTGCTAT CTGGAAAGAG   2700
AGCAAGGTGA AAAAATTATT CAGGAGTTCC TGTCCAAGGT GAAACAAATG CCCTTTACTG   2760
AAATGTCAGA AGAAAACATC ACAATAAAGT TAAAACAGCT AAAAGCTGAA GTAATAGCAA   2820
AGAATAATAG CTTTGTAAAT GAAATCATTT CACGAATAAA AGTTACTACG TGAAAAATCC   2880
CAGTAATGGA ATGAAGGTAA TATTGATAAG CTATTGTCTG TAATAGTTTT ATATTGTTTT   2940
ATATTAA                                                             2947
```

( 2 ) INFORMATION FOR SEQ ID NO:2:

( i ) SEQUENCE CHARACTERISTICS:
        ( A ) LENGTH: 934 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens ( x i ) SEQUENCE DESCRIPTION: SEQ ID NO:2:

```
Met  Ala  Val  Gln  Pro  Lys  Glu  Thr  Leu  Gln  Leu  Glu  Ser  Ala  Ala  Glu
 1                  5                      10                      15

Val  Gly  Phe  Val  Arg  Phe  Phe  Gln  Gly  Met  Pro  Glu  Lys  Pro  Thr  Thr
                    20                      25                      30

Thr  Val  Arg  Leu  Phe  Asp  Arg  Gly  Asp  Phe  Tyr  Thr  Ala  His  Gly  Glu
               35                      40                      45

Asp  Ala  Leu  Leu  Ala  Ala  Arg  Glu  Val  Phe  Lys  Thr  Gln  Gly  Val  Ile
     50                      55                      60

Lys  Tyr  Met  Gly  Pro  Ala  Gly  Ala  Lys  Asn  Leu  Gln  Ser  Val  Val  Leu
65                       70                      75                       80

Ser  Lys  Met  Asn  Phe  Glu  Ser  Phe  Val  Lys  Asp  Leu  Leu  Leu  Val  Arg
                    85                      90                      95

Gln  Tyr  Arg  Val  Glu  Val  Tyr  Lys  Asn  Arg  Ala  Gly  Asn  Lys  Ala  Ser
               100                     105                     110

Lys  Glu  Asn  Asp  Trp  Tyr  Leu  Ala  Tyr  Lys  Ala  Ser  Pro  Gly  Asn  Leu
               115                     120                     125

Ser  Gln  Phe  Glu  Asp  Ile  Leu  Phe  Gly  Asn  Asn  Asp  Met  Ser  Ala  Ser
     130                     135                     140

Ile  Gly  Val  Val  Gly  Val  Lys  Met  Ser  Ala  Val  Asp  Gly  Gln  Arg  Gln
145                      150                     155                      160

Val  Gly  Val  Gly  Tyr  Val  Asp  Ser  Ile  Gln  Arg  Lys  Leu  Gly  Leu  Cys
                    165                     170                     175

Glu  Phe  Pro  Asp  Asn  Asp  Gln  Phe  Ser  Asn  Leu  Glu  Ala  Leu  Leu  Ile
               180                     185                     190

Gln  Ile  Gly  Pro  Lys  Glu  Cys  Val  Leu  Pro  Gly  Gly  Glu  Thr  Ala  Gly
               195                     200                     205

Asp  Met  Gly  Lys  Leu  Arg  Gln  Ile  Ile  Gln  Arg  Gly  Gly  Ile  Leu  Ile
     210                     215                     220

Thr  Glu  Arg  Lys  Lys  Ala  Asp  Phe  Ser  Thr  Lys  Asp  Ile  Tyr  Gln  Asp
225                      230                     235                      240

Leu  Asn  Arg  Leu  Leu  Lys  Gly  Lys  Lys  Gly  Glu  Gln  Met  Asn  Ser  Ala
                    245                     250                     255

Val  Leu  Pro  Glu  Met  Glu  Asn  Gln  Val  Ala  Val  Ser  Ser  Leu  Ser  Ala
               260                     265                     270

Val  Ile  Lys  Phe  Leu  Glu  Leu  Leu  Ser  Asp  Asp  Ser  Asn  Phe  Gly  Gln
               275                     280                     285

Phe  Glu  Leu  Thr  Thr  Phe  Asp  Phe  Ser  Gln  Tyr  Met  Lys  Leu  Asp  Ile
     290                     295                     300

Ala  Ala  Val  Arg  Ala  Leu  Asn  Leu  Phe  Gln  Gly  Ser  Val  Glu  Asp  Thr
305                      310                     315                      320

Thr  Gly  Ser  Gln  Ser  Leu  Ala  Ala  Leu  Leu  Asn  Lys  Cys  Lys  Thr  Pro
```

-continued

|  |  |  | 325 |  |  |  | 330 |  |  |  | 335 |  |  |
|---|---|---|---|---|---|---|---|---|---|---|---|---|---|
| Gln | Gly | Gln | Arg | Leu | Val | Asn | Gln | Trp | Ile | Lys | Gln | Pro | Leu | Met | Asp |
|  |  |  | 340 |  |  |  | 345 |  |  |  | 350 |  |  |
| Lys | Asn | Arg | Ile | Glu | Glu | Arg | Leu | Asn | Leu | Val | Glu | Ala | Phe | Val | Glu |
|  |  | 355 |  |  |  | 360 |  |  |  | 365 |  |  |  |
| Asp | Ala | Glu | Leu | Arg | Gln | Thr | Leu | Gln | Glu | Asp | Leu | Leu | Arg | Arg | Phe |
|  | 370 |  |  |  | 375 |  |  |  | 380 |  |  |  |  |
| Pro | Asp | Leu | Asn | Arg | Leu | Ala | Lys | Lys | Phe | Gln | Arg | Gln | Ala | Ala | Asn |
| 385 |  |  |  | 390 |  |  |  | 395 |  |  |  | 400 |
| Leu | Gln | Asp | Cys | Tyr | Arg | Leu | Tyr | Gln | Gly | Ile | Asn | Gln | Leu | Pro | Asn |
|  |  |  | 405 |  |  |  | 410 |  |  |  | 415 |  |
| Val | Ile | Gln | Ala | Leu | Glu | Lys | His | Glu | Gly | Lys | His | Gln | Lys | Leu | Leu |
|  |  | 420 |  |  |  | 425 |  |  |  | 430 |  |  |
| Leu | Ala | Val | Phe | Val | Thr | Pro | Leu | Thr | Asp | Leu | Arg | Ser | Asp | Phe | Ser |
|  |  | 435 |  |  |  | 440 |  |  |  | 445 |  |  |
| Lys | Phe | Gln | Glu | Met | Ile | Glu | Thr | Thr | Leu | Asp | Met | Asp | Gln | Val | Glu |
|  | 450 |  |  |  | 455 |  |  |  | 460 |  |  |  |
| Asn | His | Glu | Phe | Leu | Val | Lys | Pro | Ser | Phe | Asp | Pro | Asn | Leu | Ser | Glu |
| 465 |  |  |  | 470 |  |  |  | 475 |  |  |  | 480 |
| Leu | Arg | Glu | Ile | Met | Asn | Asp | Leu | Glu | Lys | Lys | Met | Gln | Ser | Thr | Leu |
|  |  |  | 485 |  |  |  | 490 |  |  |  | 495 |
| Ile | Ser | Ala | Ala | Arg | Asp | Leu | Gly | Leu | Asp | Pro | Gly | Lys | Gln | Ile | Lys |
|  |  | 500 |  |  |  | 505 |  |  |  | 510 |  |  |
| Leu | Asp | Ser | Ser | Ala | Gln | Phe | Gly | Tyr | Tyr | Phe | Arg | Val | Thr | Cys | Lys |
|  |  | 515 |  |  |  | 520 |  |  |  | 525 |  |  |
| Glu | Glu | Lys | Val | Leu | Arg | Asn | Asn | Lys | Asn | Phe | Ser | Thr | Val | Asp | Ile |
|  | 530 |  |  |  | 535 |  |  |  | 540 |  |  |  |
| Gln | Lys | Asn | Gly | Val | Lys | Phe | Thr | Asn | Ser | Lys | Leu | Thr | Ser | Leu | Asn |
| 545 |  |  |  | 550 |  |  |  | 555 |  |  |  | 560 |
| Glu | Glu | Tyr | Thr | Lys | Asn | Lys | Thr | Glu | Tyr | Glu | Glu | Ala | Gln | Asp | Ala |
|  |  |  | 565 |  |  |  | 570 |  |  |  | 575 |
| Ile | Val | Lys | Glu | Ile | Val | Asn | Ile | Ser | Ser | Gly | Tyr | Val | Glu | Pro | Met |
|  |  |  | 580 |  |  |  | 585 |  |  |  | 590 |  |
| Gln | Thr | Leu | Asn | Asp | Val | Leu | Ala | Gln | Leu | Asp | Ala | Val | Val | Ser | Phe |
|  |  | 595 |  |  |  | 600 |  |  |  | 605 |  |  |
| Ala | His | Val | Ser | Asn | Gly | Ala | Pro | Val | Pro | Tyr | Val | Arg | Pro | Ala | Ile |
|  | 610 |  |  |  | 615 |  |  |  | 620 |  |  |  |
| Leu | Glu | Lys | Gly | Gln | Gly | Arg | Ile | Ile | Leu | Lys | Ala | Ser | Arg | His | Ala |
| 625 |  |  |  | 630 |  |  |  | 635 |  |  |  | 640 |
| Cys | Val | Glu | Val | Gln | Asp | Glu | Ile | Ala | Phe | Ile | Pro | Asn | Asp | Val | Tyr |
|  |  |  | 645 |  |  |  | 650 |  |  |  | 655 |
| Phe | Glu | Lys | Asp | Lys | Gln | Met | Phe | His | Ile | Ile | Thr | Gly | Pro | Asn | Met |
|  |  |  | 660 |  |  |  | 665 |  |  |  | 670 |  |
| Gly | Gly | Lys | Ser | Thr | Tyr | Ile | Arg | Gln | Thr | Gly | Val | Ile | Val | Leu | Met |
|  |  |  | 675 |  |  |  | 680 |  |  |  | 685 |  |
| Ala | Gln | Ile | Gly | Cys | Phe | Val | Pro | Cys | Glu | Ser | Ala | Glu | Val | Ser | Ile |
|  | 690 |  |  |  | 695 |  |  |  | 700 |  |  |  |
| Val | Asp | Cys | Ile | Leu | Ala | Arg | Val | Gly | Ala | Gly | Asp | Ser | Gln | Leu | Lys |
| 705 |  |  |  | 710 |  |  |  | 715 |  |  |  | 720 |
| Gly | Val | Ser | Thr | Phe | Met | Ala | Glu | Met | Leu | Glu | Thr | Ala | Ser | Ile | Leu |
|  |  |  | 725 |  |  |  | 730 |  |  |  | 735 |
| Arg | Ser | Ala | Thr | Lys | Asp | Ser | Leu | Ile | Ile | Ile | Asp | Glu | Leu | Gly | Arg |
|  |  | 740 |  |  |  | 745 |  |  |  | 750 |  |  |

| | Gly | Thr | Ser | Thr | Tyr | Asp | Gly | Phe | Gly | Leu | Ala | Trp | Ala | Ile | Ser | Glu |
|---|---|---|---|---|---|---|---|---|---|---|---|---|---|---|---|---|
| | | | 755 | | | | 760 | | | | | | 765 | | | |
| | Tyr | Ile | Ala | Thr | Lys | Ile | Gly | Ala | Phe | Cys | Met | Phe | Ala | Thr | His | Phe |
| | | 770 | | | | 775 | | | | | | 780 | | | | |
| | His | Glu | Leu | Thr | Ala | Leu | Ala | Asn | Gln | Ile | Pro | Thr | Val | Asn | Asn | Leu |
| | 785 | | | | 790 | | | | | 795 | | | | | | 800 |
| | His | Val | Thr | Ala | Leu | Thr | Thr | Glu | Glu | Thr | Leu | Thr | Met | Leu | Tyr | Gln |
| | | | | | 805 | | | | 810 | | | | | | 815 | |
| | Val | Lys | Lys | Gly | Val | Cys | Asp | Gln | Ser | Phe | Gly | Ile | His | Val | Ala | Glu |
| | | | | 820 | | | | 825 | | | | | 830 | | | |
| | Leu | Ala | Asn | Phe | Pro | Lys | His | Val | Ile | Glu | Cys | Ala | Lys | Gln | Lys | Ala |
| | | | 835 | | | | 840 | | | | | 845 | | | | |
| | Leu | Glu | Leu | Glu | Glu | Phe | Gln | Tyr | Ile | Gly | Glu | Ser | Gln | Gly | Tyr | Asp |
| | 850 | | | | | 855 | | | | 860 | | | | | | |
| | Ile | Met | Glu | Pro | Ala | Ala | Lys | Lys | Cys | Tyr | Leu | Glu | Arg | Glu | Gln | Gly |
| | 865 | | | | 870 | | | | 875 | | | | | | | 880 |
| | Glu | Lys | Ile | Ile | Gln | Glu | Phe | Leu | Ser | Lys | Val | Lys | Gln | Met | Pro | Phe |
| | | | | 885 | | | | | 890 | | | | | 895 | | |
| | Thr | Glu | Met | Ser | Glu | Glu | Asn | Ile | Thr | Ile | Lys | Leu | Lys | Gln | Leu | Lys |
| | | | | 900 | | | | | 905 | | | | | 910 | | |
| | Ala | Glu | Val | Ile | Ala | Lys | Asn | Asn | Ser | Phe | Val | Asn | Glu | Ile | Ile | Ser |
| | | | 915 | | | | 920 | | | | | 925 | | | | |
| | Arg | Ile | Lys | Val | Thr | Thr |
| | | | 930 | | | |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CTGGATCCAC NGGNCCNAAY ATG  23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CTGGATCCRT ARTGNGTNRC RAA  23

( 2 ) INFORMATION FOR SEQ ID NO:5:

( i ) SEQUENCE CHARACTERISTICS:
        ( A ) LENGTH: 19 base pairs
        ( B ) TYPE: nucleic acid (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

CCACAATGGA CACTTCTGC                                                                            19

(2) INFORMATION FOR SEQ ID NO:6:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (xi) SEQUENCE DESCRIPTION: SEQ ID NO:6:

CACCTGTTCC ATATGTACG                                                                            19

(2) INFORMATION FOR SEQ ID NO:7:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

AAAATGGGTT GCAAACATGC                                                                           20

(2) INFORMATION FOR SEQ ID NO:8:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GTGATAGTAC TCATGGCCC                                                                            19

(2) INFORMATION FOR SEQ ID NO:9:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

AGATCTTCTT CTGGTTCGTC                                                                    20

(2) INFORMATION FOR SEQ ID NO:10:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

GCCAACAATA ATTTCTGGTG                                                                    20

(2) INFORMATION FOR SEQ ID NO:11:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

TGGATAAGAA CAGAATAGAG G                                                                  21

(2) INFORMATION FOR SEQ ID NO:12:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

CCACAATGGA CACTTCTGC                                                                     19

(2) INFORMATION FOR SEQ ID NO:13:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

CACCTGTTCC ATATGTACG                                                              19

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

AAAATGGGTT GCAAACATGC                                                             20

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

GTGATAGTAC TCATGGCCC                                                              19

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GACAATAGCT TATCAATATT ACC                                                         23